US007217542B2

(12) United States Patent
Tyvoll et al.

(10) Patent No.: US 7,217,542 B2

(45) Date of Patent: May 15, 2007

(54) MICROFLUIDIC SYSTEM FOR ANALYZING NUCLEIC ACIDS

(75) Inventors: David Tyvoll, La Jolla, CA (US); Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 629 days.

(21) Appl. No.: 10/286,104

(22) Filed: Oct. 31, 2002

(65) Prior Publication Data

US 2004/0086870 A1 May 6, 2004

(51) Int. Cl.
*C12P 19/34* (2006.01)
*C12Q 1/64* (2006.01)

(52) U.S. Cl. .......................................... 435/91.1; 435/6

(58) Field of Classification Search .................... 257/1, 257/4, 5; 422/68.1, 50; 436/6, 91.1, 91.2; 536/23.1, 24.3, 24.33; 435/6, 91.1, 91.2
See application file for complete search history.

(56) References Cited

U.S. PATENT DOCUMENTS

| | | | |
|---|---|---|---|
| 5,374,524 A | 12/1994 | Miller | |
| 5,436,129 A | 7/1995 | Stapleton | |
| 5,451,500 A | 9/1995 | Stepleton | |
| 5,500,356 A | 3/1996 | Li et al. | |
| 5,591,580 A | 1/1997 | Bergmeyer et al. | |
| 5,700,644 A | 12/1997 | Gould et al. | |
| 5,759,773 A | 6/1998 | Tyagi et al. | |
| 5,776,672 A | 7/1998 | Hashimoto et al. | |
| 5,851,772 A | 12/1998 | Mirzabekov et al. | |
| 5,910,406 A | 6/1999 | Minter | |
| 5,955,351 A | 9/1999 | Gerdes et al. | |
| 5,958,738 A | 9/1999 | Lindemann et al. | |
| 6,030,781 A | 2/2000 | Shieh | |
| 6,060,245 A | 5/2000 | Sorge et al. | |
| 6,203,981 B1 | 3/2001 | Ackley et al. | |
| 6,238,624 B1 | 5/2001 | Heller et al. | |
| 6,261,771 B1 | 7/2001 | Bohannon | |
| 6,264,814 B1 | 7/2001 | Lange | |
| 6,344,326 B1 | 2/2002 | Nelson et al. | |
| 6,391,624 B1 | 5/2002 | Megerle | |
| 6,403,338 B1 | 6/2002 | Knapp et al. | |
| 6,406,857 B1 | 6/2002 | Shuber et al. | |
| 6,423,536 B1 | 7/2002 | Jovanovich et al. | |
| 6,729,352 B2 * | 5/2004 | O'Connor et al. | 137/827 |
| 2002/0037499 A1 * | 3/2002 | Quake et al. | 435/5 |
| 2002/0155586 A1 | 10/2002 | Cheng et al. | |

FOREIGN PATENT DOCUMENTS

| | | |
|---|---|---|
| WO | WO 99/29711 | 6/1999 |
| WO | WO 02/24949 | 3/2002 |

* cited by examiner

*Primary Examiner*—Young J. Kim

(57) ABSTRACT

A system, including methods and apparatus, for microfluidic analysis of a nucleic acid target in a nucleic acid mixture. The system includes a method to preselect the target from the mixture before amplification. Preselection enriches the mixture for the target by retaining the target on a target-selective receptor and then removing unretained non-target nucleic acids. The preselected target then may be amplified from the enriched mixture and assayed. Devices configured to carry out the method are also disclosed.

21 Claims, 9 Drawing Sheets

MICROFLUIDIC SYSTEM FOR ANALYZING NUCLEIC ACIDS

BACKGROUND

Rapid progress in genomic sequencing and proteomics has pushed the biotechnology sector to develop faster and more efficient devices for analyzing nucleic acids in biological samples. Accordingly, the biotechnology sector has directed substantial effort toward developing miniaturized microfluidic devices, often termed labs-on-a-chip, for sample analysis. Such devices may analyze samples in very small volumes of fluid, providing more economical use of reagents and samples, and in some cases dramatically speeding up assays. These devices offer the future possibility of human health assessment, genetic screening, and pathogen detection, among others, as routine, relatively low-cost procedures carried out very rapidly in a clinical setting or in the field.

Despite the potential of microfluidics, the analysis of low quantities of dilute target nucleic acids poses substantial technical problems for microfluidic devices. A typical nucleic acid analysis relies on nonselective isolation of all nucleic acids during initial sample processing. Then, a nucleic acid target(s) may be selectively amplified, generally in the presence of all of the isolated nucleic acids, to allow subsequent assay of the amplified target. However, in many cases the target is isolated in a relatively dilute form during initial sample processing and represents only a tiny fraction of the total isolated nucleic acids. For example, clinically relevant levels of human pathogens may correspond to substantially fewer than one particle or organism per microliter of human blood. Furthermore, a genetic region of interest from a low-titer pathogen or a single-copy gene may represent less than one-millionth of the total DNA isolated from a mammalian sample.

A dilute target that makes up a small fraction of the isolated nucleic acids in a sample may pose at least two problems for amplification of the target. First, because the target is dilute, a relatively large chamber, for example, up to one-hundred microliters or more, may be necessary to hold a fluid volume large enough to include a detectable number of target molecules. As a result, the need for input of a detectable number of target molecules may necessitate additional sample processing before amplification or even preclude the use of some types of microfluidic devices, particularly those that amplify and assay target nucleic acids in sub-microliter volumes. By contrast, a dilute sample in a large volume loses the benefit of microfluidic devices. Second, because the target often represents a tiny fraction of all isolated nucleic acids in the sample, amplification efficiency is reduced by the excess of non-target nucleic acids. For example, side reactions with non-target nucleic acids may slow the rate of target amplification and deplete amplification reagents, resulting at least in a decrease in signal-to-noise ratio or even a complete absence of target signal.

SUMMARY

A system is provided, including methods and apparatus, for microfluidic analysis of a nucleic acid target in a nucleic acid mixture. The system includes a method to preselect the target from the mixture before amplification. Preselection enriches the mixture for the target by retaining the target on a target-selective receptor and then removing unretained non-target nucleic acids. The preselected target then may be amplified from the enriched mixture and assayed. Devices configured to carry out the method are also disclosed.

DETAILED DESCRIPTION

Figure 1:
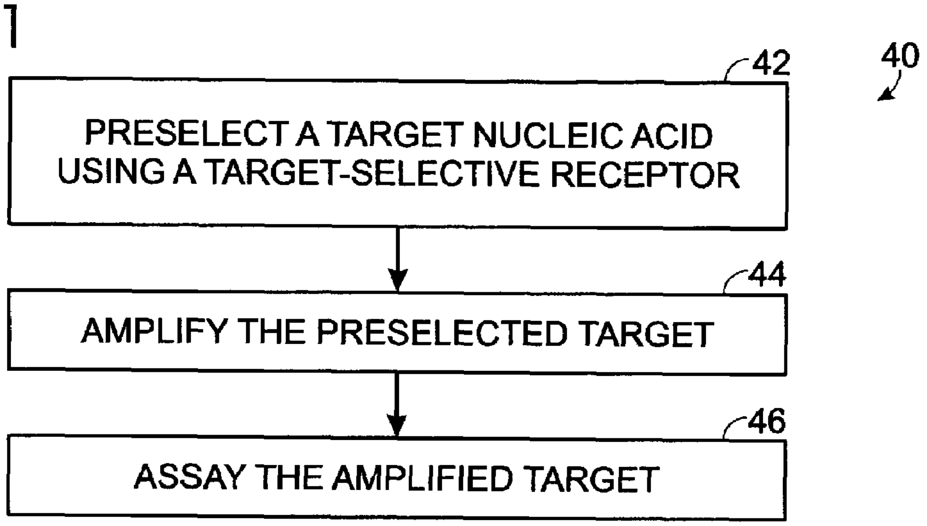
FIG. 1 is a flowchart illustrating an exemplary method for analyzing a nucleic acid target using preselection followed by amplification of the preselected target, in accordance with an embodiment of the invention.

Systems, including methods and apparatus, are provided for microfluidic analysis of nucleic acids. The systems provide for preselecting a nucleic acid target from a mixture of the target and non-target nucleic acids. During preselection, the target is at least partially purified from non-target nucleic acids, and also may be concentrated.

The preselection method may include some or all of the following steps. The nucleic mixture may be introduced into a microfluidic chamber. In the chamber the mixture may be attracted to an electrode(s), for example, an electrode included in electronics formed on a substrate. Target molecules from the attracted mixture are bound selectively by a receptor (or receptors) immobilized near, and generally connected to, the electrode. By contrast, non-target nucleic acids remain substantially unbound. The mixture then may be enriched for the target by removing unbound nucleic acids, for example, by bulk fluid flow or electrokinetic movement of unretained nucleic acids, among others. Subsequently, the target of the enriched mixture may be released from the receptor for further processing by any suitable physical, electrical, and/or chemical treatment.

The preselected target may be amplified and then assayed. Amplification may be conducted in the same or a distinct microfluidic chamber. Because the non-target nucleic acids are substantially removed by preselection, amplification may be conducted more efficiently, with fewer side reactions caused by the non-target nucleic acids. In addition, less-stringent amplification conditions may be used in some embodiments, for example, to allow amplification of distinct target species. Following amplification, the amplified target may be assayed directly or through binding to a receptor. The assay receptor may be the same as, or distinct from, the preselection receptor. In either case, the assay receptor may allow the target assay to be performed with the same stringency or higher stringency than preselection, for example, by altering electric field strength, temperature, or chemical stringency. With higher stringency, the preselected target may be resolved into plural related but distinct species, for example, to analyze gene polymorphisms. Therefore, the methods and devices described herein may allow more sensitive and/or accurate analysis of nucleic acids with dilute and/or complex samples.

Further aspects are provided in the following sections: (I) preselection-assisted analysis of nucleic acids, (II) microfluidic analysis with an integrated cartridge, (III) microfluidic systems, (IV) samples, and (V) assays.

I. Preselection—Assisted Analysis of Nucleic Acids

This section describes a microfluidic system for preselection-assisted analysis of nucleic acids. Preselection enriches a nucleic acid mixture for a nucleic acid target (or targets) by at least partially removing non-target nucleic acids. The preselected target may be further selected, that is, selectively amplified and assayed, with greater efficiency because of reduced interference from the non-target nucleic acids. Exemplary methods and devices for preselection-assisted analysis are described below in this section. A cartridge embodiment for preselection-assisted analysis is described below in Section II.

FIG. 1 shows a flow diagram of a method 40 for preselection-assisted analysis of nucleic acids. A nucleic acid target may be preselected using a target-selective receptor, as shown at 42. Preselection may enrich a nucleic acid mixture for the target relative to non-target nucleic acids by removing non-target nucleic acids of the mixture so that the target is at least partially purified. In addition, preselection may reduce the amount of fluid in which the target is carried, thereby concentrating the target for subsequent selective reaction(s) and/or assay, termed selection. For example, the preselected target may be selectively amplified, as shown at 44, to increase the total number of target-related molecules. Amplification may be conducted using any of the reagents, methods, and/or devices described below in Sections II–V. The amplified target then may be assayed, as shown at 46, for example, using any of the assay procedures described below in Section II or V. In particular, the amplified target may be assayed selectively by contacting a positioned receptor or receptor array with the amplified target, for example, in an assay chamber of a microfluidic cartridge (see FIGS. 11–17). Binding of the amplified target to the receptor or receptor array then may be measured.

Figure 2:
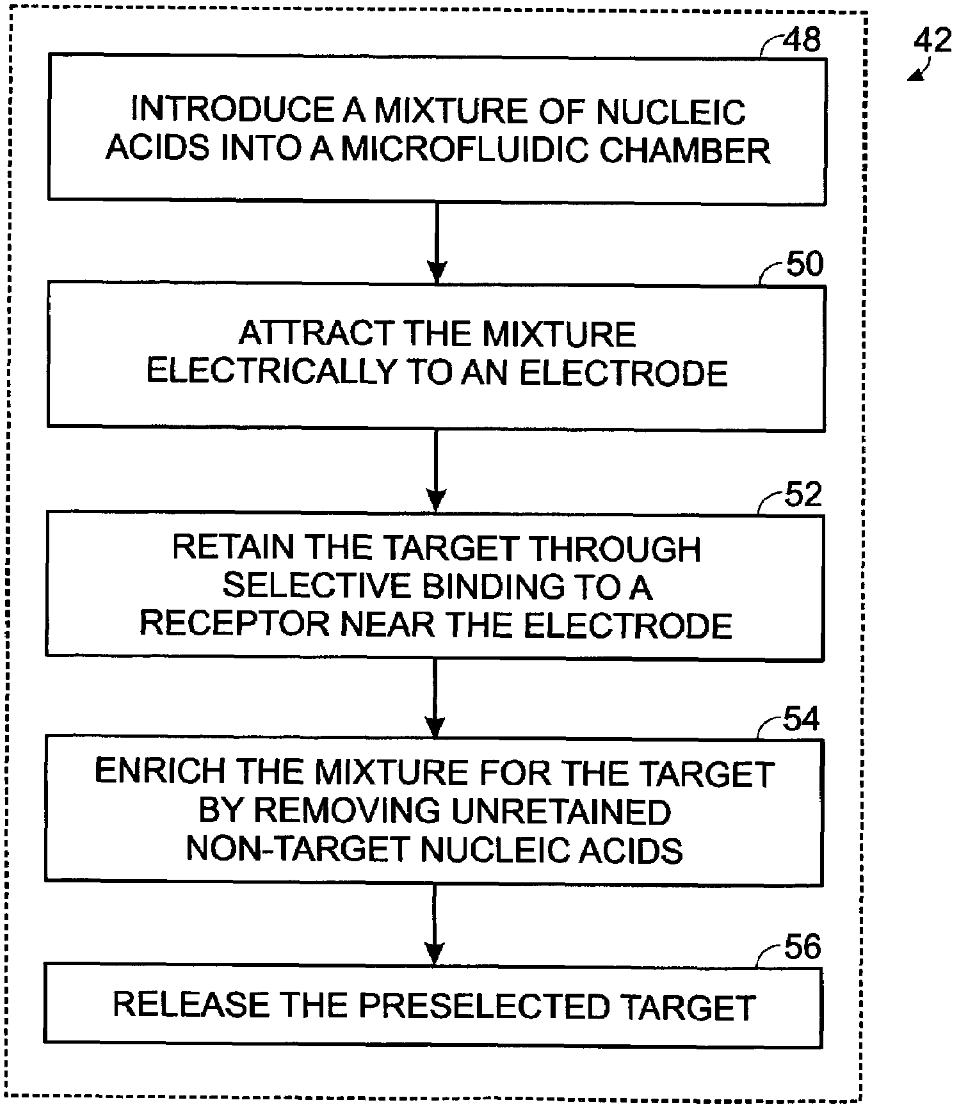
FIG. 2 is a flowchart illustrating an exemplary method for performing the preselection portion of the flowchart in FIG. 1.

FIG. 2 shows a flow diagram for a method 42 of preselecting nucleic acid target. Method 42 is included as a step in method 40 of FIG. 1.

A mixture of nucleic acids, including a nucleic acid target, may be introduced into a microfluidic chamber, as shown at 48. The mixture may be produced by pre-processing a sample within a microfluidic device to isolate nucleic acids, as described in Section II, or may be pre-processed external to the device, for example, by automated or manual sample manipulation. Suitable samples may include any of the samples described below in Section IV. The mixture may be introduced by bulk fluid flow, such as by mechanically driven flow. Alternatively, the mixture may be introduced by electrokinetic movement of fluid and/or nucleic acids, as described in Section III, or by any other suitable pumping mechanism(s).

Next, the mixture may be attracted electrically to an electrode, as shown at 50. The electrode may be included in electronics formed on a substrate, and may be a single electrode or plural electrodes. Control of the electronics, for example, by an electrically coupled control apparatus (see FIG. 7 of Section II) allows each electrode to be electrically biased or unbiased. When biased positively, the electrode attracts negatively charged nucleic acids in an electric field extending from the electrode, thereby electrically concentrating the mixture (and the target) near the electrode.

The target then may be retained through binding to a receptor disposed near the electrode, as shown at 52. As used herein, a retained target is retained relative to non-target nucleic acids, that is, selectively held in place by binding to the receptor. Speed and/or efficiency of target binding to the receptor may be related to the concentration of the target. Accordingly, the step of attracting the mixture to the electrode may improve the speed and/or efficiency of target binding.

The receptor is disposed near the electrode and may be connected to the electrode. Any suitable connection may be used, for example, by including the receptor in a layer, such as a gel, that is attached or coupled to the electrode. Alternatively, or in addition, the receptor may be chemically bonded to the electrode or attached through specific binding pair interactions, such as biotin attached to the receptor and avidin attached to the electrode (or vice versa). Other specific binding pairs that may be suitable for connecting the receptor to an electrode are listed below in Table 1 or Section V. More generally, connection between the receptor and the electrode indicates any linking relationship that holds the receptor in close proximity to the electrode during preselection.

The receptor may be any material that specifically (or selectively) interacts with the target relative to non-target nucleic acids. Exemplary receptors include nucleic acids, that is, natural or synthetic oligonucleotides, polynucleotides, or structural relatives thereof, such as peptide nucleic acids. Such nucleic acids may be configured to specifically base-pair with the target. Accordingly, a receptor may be a partially or completely single-stranded nucleic acid and may be at least substantially complementary to the target. The receptor may have a length that allows selective or specific binding, for example, a length of at least about six, ten, fifteen, or twenty nucleotides. The receptor may have any suitable GC content, length, and chemical structure to produce selective binding under the conditions with which the step of retaining is carried out. The receptor may be a single species or a mix of species disposed near and/or connected to the electrode. The mix may be a related mix, such as nucleic acids that are degenerate at one or more positions, for example, to retain one or more targets that are polymorphic, such as targets that include nucleotide polymorphisms, particularly single-nucleotide polymorphisms. Alternatively, or in addition, the mix may be an unrelated mix of receptor species that bind to spaced and/or unlinked target sequences. Further aspects of receptors are described below in Sections II and V.

In addition to selecting an appropriate structure for the receptor, selectivity (or stringency) of binding also may be adjusted by altering the conditions under which target retention occurs. Any suitable conditions may be selected, including a suitable temperature, ionic strength, solvent composition, and/or electric field strength, among others. The temperature may be adjusted by ambient temperature control of the entire microfluidic device, or by local temperature control. Such local control may be determined by electronic temperature control devices, such as thin-film heaters and temperature sensors. The ionic strength may be determined, for example, during formation of the nucleic acid mixture, and/or by electrokinetic movement of ions. Similarly, the solvent composition, such as concentration of organic solvent (for example, formamide), may be determined during formation of the mixture and/or by subsequent dilution with water or organic solvent. The interrelationship between 1) temperature at which a nucleic acid duplex separates into single strands, 2) duplex length, 3) GC content, 4) ionic strength, and 5) formamide concentration is known to those skilled in the art and/or may be determined empirically. Electronic stringency also may be used to regulate receptor-target binding (and separation), for example, by controlling the voltage and/or current applied to the electrode(s).

After target retention, the mixture may be enriched for the target by removing unretained nucleic acids, as shown at 54. Because the target is selectively retained by the receptor, non-target nucleic acids are disproportionately not bound thus not retained, that is, not held in position. Accordingly, a force applied nonselectively to the nucleic acid mixture, may selectively move the non-target nucleic acids. The force may be mechanical, to move fluid that contains the nucleic acid mixture, for example, using a fluid-handling portion of the microfluidic cartridge described in Section II. Alternatively, or in addition, the force may be electrically driven fluid and/or nucleic acid movement, or may be any other suitable force that moves nucleic acids and/or fluid. The step of enriching also may include washing the target with a wash solution, for example, to remove weakly bound and/or nonspecifically bound non-target nucleic acids.

The preselected target then may be released from binding to the receptor, as shown at 56. Release may be determined by any treatment that promotes separation of the target and receptor. Suitable treatments may include heating fluid in the chamber, for example, using electronic temperature-control devices. Alternatively, or in addition, such treatments may include, but are not limited to, changing ionic strength, solvent composition, and/or electric field strength (electronic stringency).

The released target may be selectively amplified and assayed as shown in FIG. 1 and described below in Section II. Selective amplification may be carried out using nucleic acid primers that are selective for the target. Although one or more primers may be correspond to the receptor(s) used for preselection, in some embodiments, each of the primers used for amplification is distinct from the receptor(s) used in preselection. Such distinct primers may improve the ability to selectively amplify the target relative to non-target sequences preselected by fortuitous complementarity to the receptor. In some embodiments, selective assay of the target may be determined by choice of receptor and conditions of receptor-target binding. The receptor(s) used in assaying the amplified target may be identical to, related to, or distinct from the receptor used for preselection. For example, greater selectivity may be obtained by using an assay receptor that has little or no sequence overlap with the preselection receptor. In some cases, the preselection receptor may be less selective than the assay receptor. For example, the preselection receptor may be more degenerate, shorter in length, and/or may be contacted with the target under less stringent binding conditions than the assay receptor.

FIGS. 3–6 show somewhat schematic representations of a nucleic acid mixture 60 during different stages of preselection in a microfluidic device 62 using method 42 of FIG. 2.

Figure 3:
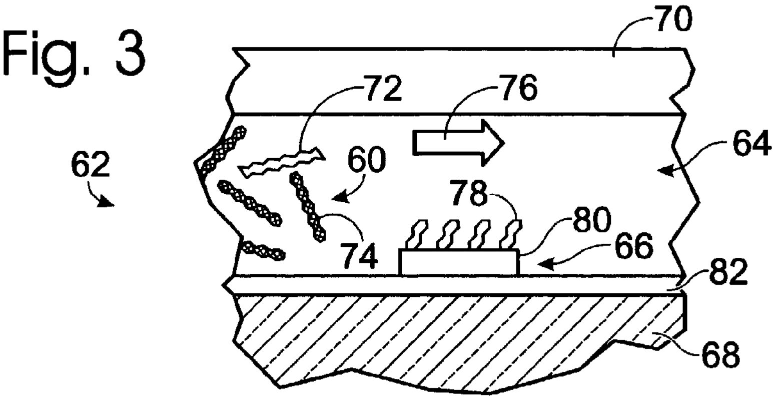
FIG. 3 is a fragmentary sectional view of an embodiment of a microfluidic device before preselection of a nucleic acid target from a nucleic acid mixture, showing the mixture being introduced to a preselection chamber.

FIG. 3 shows nucleic acid mixture 60 being introduced into a preselection chamber 64 in device 62. Chamber 64 may be any suitable fluid compartment. Here, chamber 64 is a microfluidic chamber that is partially defined by electronics 66 formed on a substrate 68. The electronics may be configured to sense and/or modify properties of fluid and/or nucleic acid in the chamber 64. The substrate may be a semiconductor or an insulator, among others The chamber also may be partially defined by a fluid barrier 70 that is attached to substrate 68 and/or electronics 66. Further aspects of substrates, electronics, fluid barriers, and fluid chambers are described below in Sections II and III.

Mixture 60 includes a nucleic acid target 72, of one or more molecules, and non-target nucleic acids 74. Non-target 74 may be in substantial excess over target 72, or at least about one-thousand-fold more abundant. Mixture 60 may be received from another portion of device 62 by mechanically driven flow, as shown at 76. Mixture 60 may be single-stranded to allow binding to a complementary single-stranded receptor 78 that is connected to electrode (or electrodes) 80 of electronics 66. With plural electrodes, each electrode may be connected to a distinct receptor or to the same receptor (or the same mix of receptors). Mixture 60 may be rendered single-stranded at any time during processing of the mixture and by any suitable duplex-denaturing mechanism. In exemplary embodiments, mixture 60 is thermally or electronically denatured in chamber 64 using electronic devices included in thin-film layers 82 of electronics 66. Alternatively, mixture 60 may be denatured chemically, thermally, and/or electrically in any other suitable portion of device 62 or external to device 62.

Figure 4:
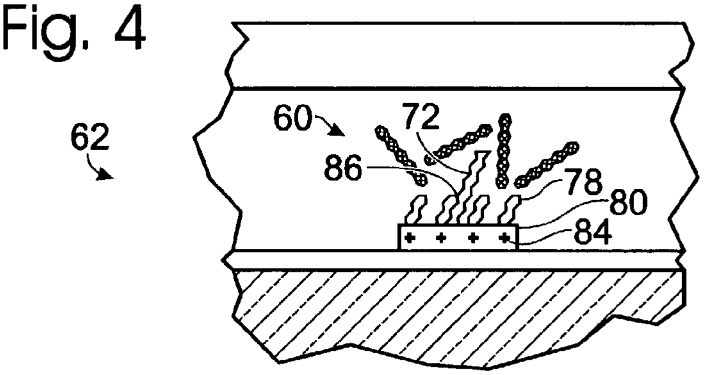
FIG. 4 is a fragmentary sectional view of the device of FIG. 3, showing the mixture being attracted to an electrode and the target being retained by binding to a target-selective receptor.

FIG. 4 shows nucleic acid mixture 60 being attracted to electrode 80. Electrode 80 may be biased positively, as shown at 84, which creates an electric field that concentrates mixture 60 proximate to electrode 80 and thus near connected receptor(s) 78.

FIG. 4 also shows target 72 being selectively retained by binding to receptor 78. Here, receptor 78 is a single-stranded oligonucleotide that basepairs selectively with target 72. Accordingly, receptor 78 and target 72 form a nucleic acid duplex 86. As shown, receptor 78 may be substantially shorter than target 72, for example, when receptor 78 is produced by chemical synthesis.

Figure 5:
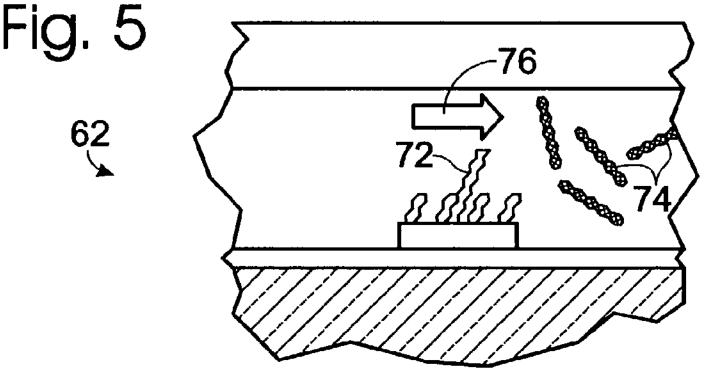
FIG. 5 is a fragmentary sectional view of the device of FIG. 3, showing the mixture being enriched by removal of unretained nucleic acids.

FIG. 5 shows mixture 60 being enriched for target 72 by removal of unretained non-target nucleic acids 74. Removal may be produced by mechanical fluid flow, as shown at 76, or by any other suitable mechanism for movement of fluid and/or charged molecules.

Figure 6:
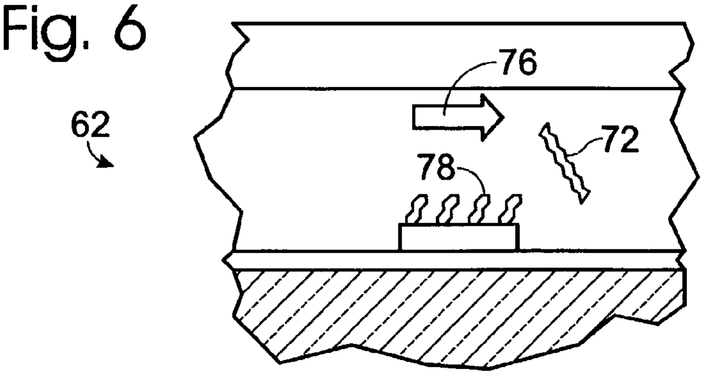
FIG. 6 is a fragmentary sectional view of the device of FIG. 3, showing the target being released.

FIG. 6 shows preselected target 72 after release from receptor 78. Release may be carried out by any suitable temperature-, chemical-, and/or electrically-based mechanism. Preselection at least partially purifies target 72 from non-target 74.

The purified target may be further processed, including amplification and assay, in preselection chamber 64 or elsewhere in device 62. For example, the purified target may be moved to another chamber for amplification and then moved back to preselection chamber 64 for assaying. In this case, receptor 78 may be used for both preselection and assay of the target, or a distinct receptor may be used for assay, either at the same or at a distinct site within chamber 64. In other embodiments, the purified target may be amplified in preselection chamber 64 and assayed in chamber 64 or in a distinct chamber.

As described more fully in Section II, mixture 60 may have a volume that is substantially larger than the volume of preselection chamber 64, so that a portion of method 42 is performed cyclically. For example, steps 48–54 of method 42 may be performed repeatedly on sequential volumes of mixture 60 held by chamber 64. Steps 48–54 may be performed in coordination with flow of mixture 72 through preselection chamber 64.

II. Microfluidic Analysis with an Integrated Cartridge

Systems, including methods and apparatus, are provided for microfluidic analysis of nucleic acids. The systems may include a cartridge configured to receive a sample(s) at an input port(s), to pre-process the sample to isolate nucleic acids, and to assay the isolated nucleic acids for one or more nucleic acids (nucleic acid species) of interest. The systems may be used to preselect, amplify, and assay target, as described in Section I. Operation of the cartridge may be controlled by a control apparatus that interfaces electrically, and, optionally, mechanically, optically, and/or acoustically with the cartridge. The cartridge may include discrete portions or devices: a fluid-handling portion for manipulating macroscopic or larger volumes of fluid and a fluidically connected, electronic assay portion for manipulating microscopic or smaller volumes of fluid. These two portions perform distinct functions. The fluid-handling portion has reservoirs that hold, deliver, route and/or receive sample and reagents, and also includes a pre-processing site that isolates nucleic acids or other analytes of interest from the sample. The fluid-handling portion delivers reagents and the isolated nucleic acids (or analytes) to the electronic assay portion, where further processing and assay of the nucleic acids may be completed electronically.

The fluid-handling portion or device may provide various interfacing features between the macroscopic world (and thus the user) and the cartridge. For example, the fluid-handling portion provides a fluid interface or input port to receive a sample, and an electrical interface for electrically coupling to a control apparatus. The fluid-handling portion also may provide a mechanical interface with the control apparatus, for example, to mechanically control valves, pumps, apply pressure, etc. Alternatively, or in addition, the fluid-handling portion may provide a user interface, to allow the microfluidic device to be grasped and handled readily for installation and removal from the control apparatus. Both the mechanical and user interfaces may be provided by a housing that forms an outer region of the fluid-handling portion.

The fluid-handling portion is configured to store and to move fluid, reagents, and/or sample directionally, in a temporally and spatially regulated fashion, through selected sections of the fluid-handling portion and assay portion. Accordingly, the fluid-handling portion may include reagent chambers for holding fluid that is used in pre-processing and/or processing the sample, waste chambers for receiving waste fluid and byproducts from either or both portions, and intermediate chambers/passages that fluidly interconnect the sample input site with the reagent and waste chambers. The intermediate chambers include a site(s) for pre-processing the sample to isolate nucleic acids from the sample.

The fluid-handling portion has a primary role in fluid manipulation. The fluid-handling portion may move reagents and sample through the fluid-handling and assay portions by mechanically driven fluid flow. Furthermore, this portion has a larger capacity for fluid than the electronic assay portion. Accordingly, the fluid-handling portion may be produced using processes and materials that provide any necessary branched and/or complex fluid-network structure. For example, the fluid-handling portion may be formed substantially from plastic using injection molding or other suitable methods. Furthermore, the fluid network of the fluid-handling portion may extend in any suitable three-dimensional configuration and is generally not constrained by a requirement to define the fluid network along a flat surface. Therefore, the fluid-handling portion may provide flexible routing of fluid through alternate pathways of various dimensions within the fluid network. In some embodiments the fluid-handling portion may define fluid paths that extend farther than two millimeters from a common plane.

The assay portion or device, also referred to as the chip portion, is fluidically connected to the fluid-handling portion and may be attached fixedly to this portion. The assay portion may not interface fluidically with the user directly, that is, the assay portion receives sample or reagents directly from the fluid-handling portion but generally not directly from the external environment.

The assay portion is configured to include electronic circuitry, also referred to as electronics, including semiconductor devices (transistors, diodes, etc.) and thin-film devices (thin-film resistors, conductors, passivation layers, etc.). Such electronic devices are formed on a base layer or substrate in the assay portion. As used herein, the term “formed on” a substrate means that the semiconductor devices and thin-film devices are created on and/or in the substrate. Suitable substrates are typically flat and may include semiconductors (such as silicon or gallium arsenide) or insulators (such as glass, ceramic, or alumina). In the case of semiconductor substrates, the semiconductor devices may be created directly in the substrate, that is, at and/or below the surface of the substrate. In the case of insulative substrates, a semiconductive layer may be coated upon the substrates, for example, as used for flat panel applications.

The substrate may perform an organizing role in the assay portion. The substrate may be attached to a fluid barrier, which may define at least one fluid compartment in conjunction with the substrate and the electronic circuitry. Because the substrate typically has a planar or flat surface, the fluid compartment and other fluid compartments defined partially by the substrate and associated electronic circuitry have a spatial configuration that may be constrained by a planar substrate geometry. The electronic circuitry, or at least a thin-film portion thereof, is disposed on a surface of the substrate, operably positioned relative to the fluid compartment, to provide electronic devices that process nucleic acid in the fluid compartment. By contrast, an opposing surface of the substrate may abut the fluid-handling portion.

The assay portion has a substantially smaller fluid capacity than the fluid-handling portion. The processing chambers formed in the assay portion may be constrained to the geometry of suitable substrates. Thus, at least some of the dimensions of the chambers in the assay portion are substantially smaller than the dimensions of fluid chambers in the fluid-handling portion, having volumes less than about 50 microliters, preferably less than 10 microliters, and even more preferably less than one microliter in volume. Accordingly, by using operably coupled electronics, processing chambers of the assay portion may use the electronics to process a sample in a volume of fluid that is many times the static fluid capacity of such chambers. For example, the assay portion may concentrate nucleic acids received in fluid from the fluid-handling portion by retaining the nucleic acids, but allowing the bulk of the fluid to return to the fluid-handling portion. Therefore, distinct portions of the cartridge may cooperate to perform distinct fluid manipulations and sample processing steps. Furthermore, aspects of the cartridge and methods described below may be used on any of the samples described in Section IV and/or using any of the assays described in Section V.

Figure 7:
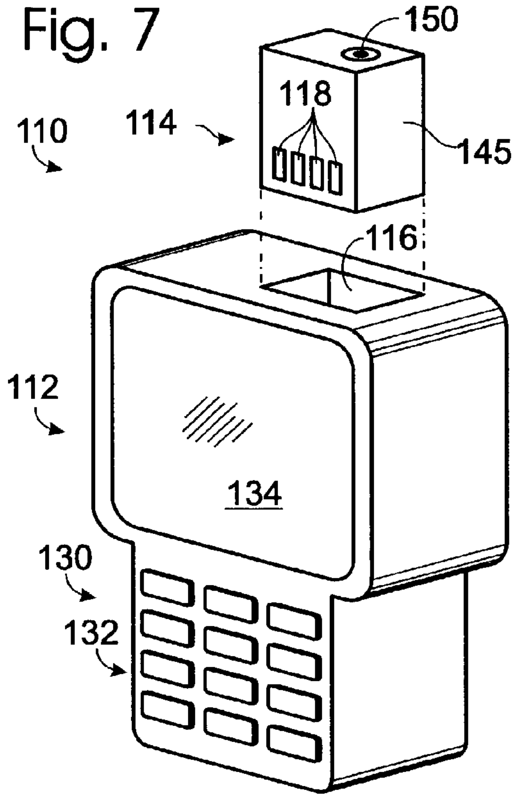
FIG. 7 is an isometric view of a microfluidic system having an integrated microfluidic cartridge aligned for mating with an exemplary control apparatus, the control apparatus being configured to power and control operation of the mated cartridge in sample processing and/or analysis, in accordance with an embodiment of the invention.
Figure 8:
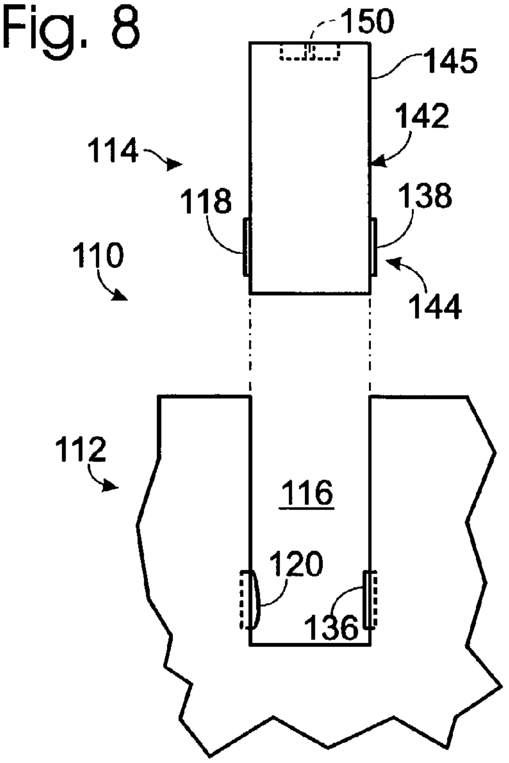
FIG. 8 is a fragmentary sectional view showing selected aspects of the cartridge and control apparatus of FIG. 7.
Figure 9:
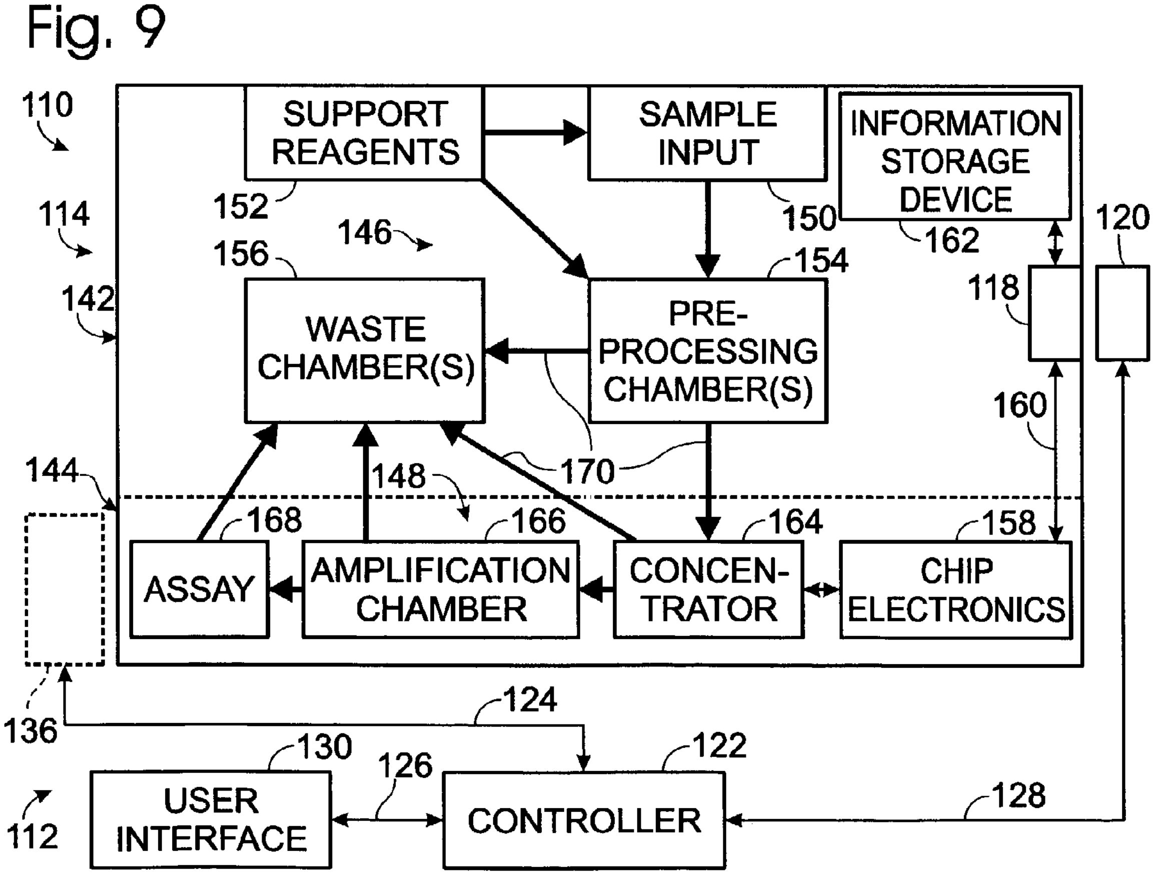
FIG. 9 is a schematic view of the cartridge and control apparatus of FIG. 7, illustrating movement of fluid, sample, electricity, digital information, and detected signals, in accordance with an embodiment of the invention.

FIGS. 7–9 show an embodiment of a microfluidic system 110 for processing and analysis of samples, particularly samples containing nucleic acids. FIGS. 7 and 8 show isometric and sectional views, respectively, of the system. FIG. 9 is a schematic representation of system 110, illustrating selected aspects of the system. System 110 includes a control apparatus 112 and an integrated cartridge 114 that is configured to be electrically coupled to control apparatus 112. In FIGS. 7 and 8, cartridge 114 is shown aligned and positioned to be received by, and thus installed in, the control apparatus. As used herein, the term “cartridge” describes a small modular unit designed to be installed in a larger control apparatus. As used herein, the term “installed in” indicates that the cartridge has been mated properly with the control apparatus, generally by at least partially inserting the cartridge in the control apparatus. Accordingly, control apparatus 112 may include a recess 116 that matingly receives cartridge 114, for example, by coupling through an electrical interface formed through contact between electrical contact pads 118 on cartridge 114 and corresponding contact structures 120 positioned in recess 116 (see FIG. 8). Alternatively, control apparatus 112 may interface electrically with cartridge 114 conductively, capacitively, and/or inductively using any other suitable structures. Control apparatus 112 may have any suitable size, for example, small enough to be held by hand, or larger for use on a bench-top or floor.

Control apparatus 112 is configured to send and receive control signals to cartridge 114, in order to control processing in cartridge 114. In some embodiments, cartridge 114 includes detection electronics. With such electronics, control apparatus receives signals from cartridge 114 that are utilized by control apparatus 112 to determine an assay result. The control apparatus may monitor and control conditions within the cartridge (such as temperature, flow rate, pressure, etc.), either through an electrical link with electronic devices within the cartridge and/or via sensors that interface with the cartridge. Alternatively, or in addition, control apparatus 112 may read information from an information storage device on the cartridge (see below) to ascertain information about the cartridge, such as reagents contained by the cartridge, assays performed by the cartridge, acceptable sample volume or type, and/or the like. Accordingly, control apparatus 112 generally provides some or all of the input and output lines described below in Section III, including power/ground lines, data input lines, fire pulse lines, data output lines, and/or clock lines, among others.

Control apparatus 112 may participate in final processing of assay data, or may transfer assay data to another device. Control apparatus 112 may interpret results, such as analysis of multiple data points (for example, from binding of a test nucleic acid to an array of receptors (see below)), and/or mathematical and/or statistical analysis of data. Alternatively, or in addition, control apparatus 112 may transfer assay data to another device, such as a centralized entity. Accordingly, control apparatus 112 may codify assay data prior to transfer.

Control apparatus 112 includes a controller 122 that processes digital information (see FIG. 9). The controller generally sends and receives electrical signals to coordinate electrical, mechanical, and/or optical activities performed by control apparatus 112 and cartridge 114, shown by double-headed arrows at 124, 126, 128.

Control apparatus 112 may communicate, shown at 126 in FIG. 9, with a user through a user interface 130. The user interface may include a keypad 132 (see FIG. 7), a screen 134, a keyboard, a touchpad, a mouse, and/or the like. The user interface typically allows the user to input and/or output data. Inputted data may be used, for example, to signal the beginning of sample processing, to halt sample processing, to input values for various processing parameters (such as times, temperatures, assays to be performed, etc.), and/or the like. Outputted data, such as stage of processing, cartridge parameters, measured results, etc. may be displayed on screen 134, sent to a printing device (not shown), stored in onboard memory, and/or sent to another digital device such as a personal computer, among others.

Control apparatus 112 also may include one or more optical, mechanical and/or fluid interfaces with cartridge 114 (see FIGS. 8 and 9). An optical interface 136 may send light to and/or receive light from cartridge 114. Optical interface 136 may be aligned with an optically transparent region 138 of cartridge 114 when the cartridge mates with control apparatus 112 (see FIG. 8 and discussion below). Accordingly, optical interface 136 may act as a detection mechanism having one or more emitters and detectors to receive optical information from the cartridge. Such optical information may relate to assay results produced by processing within the cartridge. Alternatively, or in addition, optical interface 136 may be involved in aspects of sample processing, for example, providing a light source for light-catalyzed chemical reaction, sample disruption, sample heating, etc. In any case, operation of optical interface 136 may be directed by controller 122, with corresponding measurements received by controller 122, as shown at 124 in FIG. 9, thus allowing measurements from optical interface 136 to be processed and stored electronically. Control apparatus 112 may include one or more electronically controlled mechanical interfaces (not shown), for example, to provide or regulate pressure on the cartridge. Exemplary mechanical interfaces of control apparatus 112 may include one or more valve actuators, valve regulators that control valve actuators, syringe pumps, sonicators, and/or pneumatic pressure sources, among others. In some embodiments, the control apparatus may include one or more fluid interfaces that fluidly connect the control apparatus to the cartridge. For example, the control apparatus may include fluid reservoirs that store fluid and deliver the fluid to the cartridge. However, control apparatus 112 shown here is not configured to couple fluidly to cartridge 114. Instead, in this embodiment, cartridge 114 is a closed or isolated fluid system during operation, that is, a fluid network in which fluid is not substantially added to, or removed from, the network after the sample is received. Further aspects of optical detection, and mechanical and fluid interfaces in microfluidic systems are described below in Section III.

Cartridge 114 may be configured and dimensioned as appropriate. In some embodiments, cartridge 114 is disposable, that is, intended for one-time use to analyze one sample or a set of samples (generally in parallel). Cartridge 114 may have a size dictated by assays to be performed, fluid volumes to be manipulated, nonfluid volume of the cartridge, and so on. However, cartridge 114 typically is small enough to be easily grasped and manipulated with one hand (or smaller).

Cartridge 114 typically includes at least two structurally and functionally distinct components: a fluid-handling portion 142 and an assay (or chip) portion 144. Fluid-handling portion may include a housing 145 that forms an outer mechanical interface with the control apparatus, for example, to operate valves and pumps. Housing may define the structure of interior fluid compartments. Housing 145 also substantially may define the external structure of the cartridge and thus may provide a gripping surface for handling by a user. Assay portion 144 may be attached fixedly to fluid-handling portion 142, for example, on an exterior or interior surface of fluid-handling portion 142. External attachment of assay portion 144 may be suitable, for example, when results are measured optically, such as with optical interface 136. Internal and/or external attachment may be suitable when results are measured electrically, or when fluid-handling portion 142 is optically transparent. Assay portion 144 also typically is connected fluidically to fluid-handling portion 142, as described below, to allow exchange of fluid between these two portions.

Fluid-handling portion 142 thus may be configured to receive fluids from external the cartridge, store the fluids, and deliver the fluids to fluid compartments in both fluid-handling portion 142 and assay portion 144, for example, by mechanically driven fluid flow. Accordingly, fluid-handling portion may define a fluid network 146 with a fluid capacity (volume) that is substantially larger than a corresponding fluid network (or fluid space) 148 of assay portion 144. Each fluid network may have one fluid compartment, or more typically, plural fluidically connected fluid compartments, generally chambers connected by fluid conduits.

Fluid-handling portion 142 includes a sample input site or port 150. Sample input site 150 is generally externally accessible but may be sealable after sample is introduced to the site. Cartridge 114 is shown to include one sample input site 150, but any suitable number of sample input sites may be included in fluid-handling portion 142.

Fluid-handling portion 142 also includes one or more reagent reservoirs (or fluid storage chambers) 152 to carry support reagents (see FIG. 9). Reagent reservoirs 152 each may be externally accessible, to allow reagent loading after the fluid-handling portion has been manufactured. Alternatively, some or all of reagent reservoirs 152 may be loaded with reagent during manufacturing. Support reagents generally include any fluid solution or mixture involved in sample processing, analysis, and/or general operation of cartridge 114.

Fluid-handling portion 142 also may include one or more additional chambers, such as a pre-processing chamber(s) 154 and/or a waste chamber(s) 156. Pre-processing chamber(s) 154 and waste chamber(s) 156 may be accessible only internally, for example, through sample input site 150 and/or reagent reservoirs 152, or one or more may be externally accessible to a user. Pre-processing chamber(s) are fluid passages configured to modify the composition of a sample, generally in cooperation with fluid flow. For example, such passages may isolate analytes (such as nucleic acids) from inputted sample, that is, at least partially separating analyte from waste material or a waste portion of the sample, as described below. Further aspects of fluid-handling portions are described below in Section III.

In a preferred embodiment, the fluid-handling portion 142 and in fact all fluid compartments of cartridge 114 are sealed against customer access, except for the sample input 150. This sealing may operate to avoid potential contamination of reagents, to assure safety, and/or to avoid loss of fluids from fluid-handling portion 142. Some of the reagents and/or processing byproducts resultant from pre-processing and/or additional processing may be toxic or otherwise hazardous to the user if the reagents or byproducts leak out and/or come in contact with the user. Furthermore, some of the reagents may be very expensive and hence in minimal supply in cartridge 114. Thus, the preferred implementation of cartridge 114 is an integral, sealed, disposable cartridge with a fluid interface(s) only for sample input 150, an electrical interface 118, and optional mechanical, optical and/or acoustic interfaces.

Assay portion 144 is configured for further processing of nucleic acid in fluid network 148 after nucleic acid isolation in fluid-handling portion 142. Accordingly, assay portion 144 relies on electronics or electronic circuitry 158, which may include thin-film electronic devices to facilitate controlled processing of nucleic acids received from fluid-handling portion 142. By contrast, bulk fluid flow in assay portion 144 may be mediated by mechanically driven flow of fluid from fluid-handling portion 142, through assay portion 144, and back to portion 142.

Electronic circuitry 158 of the assay portion may include thin-film electronic devices to modify and/or sense fluid and/or analyte properties. Exemplary roles of such thin-film devices may include concentrating and/or preselecting the isolated nucleic acids, moving the nucleic acids to different reaction chambers and/or assay sites, controlling reaction conditions (such as during amplification, hybridization to receptors, denaturation of double-stranded nucleic acids, etc.), and/or the like (see Section III also). The thin-film devices may be operably coupled to any regions of fluid network 148. Operably coupled may include direct contact with fluid, for example, with electrodes, or spaced from fluid by one or more insulating thin-film layers (see below). In either case, the operably disposed devices may be disposed near the surface of the substrate (see below). Further aspects of the electronic circuitry, thin-film layers, and substrates are described below in this section and in Section III.

Electronic circuitry 158 of assay portion 144 is controlled, at least in part, by electrically coupling to control apparatus 112. For example, as shown in FIG. 9, controller 122 may be coupled, shown at 128, via contact structures 120, with contact pads 118 disposed on fluid-handling portion 142 of cartridge 114. In turn, contact pads 118 may be electrically coupled with electronic circuitry 158, as shown at 160. One or more additional integrated circuits, or interface circuits, may be coupled electrically to contact pads 118 intermediate to circuitry 158, for example, to allow circuitry 158 to have greater complexity and/or to minimize the number of distinct contact pads (or sites) on cartridge 114. Thus, the contact pads alone or in combination with the interface circuits form an interconnect circuit that electrically couples the electronics to the controller when the cartridge is installed in the control apparatus. Contact pads also may couple to an electronic information storage device 162 carried in cartridge 114, for example, in fluid-handling portion 142, as shown. The information storage device may store information that relates to the cartridge, such as fluid network configurations, reservoir contents, assay capabilities, assay parameters, and/or the like. In alternative embodiments, contact pads 118 or other electrical coupling structures may be disposed on assay portion 144 instead of, or in addition to, being included in fluid-handling portion 142.

Assay portion 144 typically is configured to carry out nucleic acid processing in fluid network 148, at least partially by operation of circuitry 158. Here, fluid network 148 is shown to include three functional regions: a concentrator 164, an amplification chamber 166, and an assay chamber 168. As described in more detail below, each of these functional regions may include electrodes to facilitate nucleic acid retention and release (and thus concentration), and/or directed movement toward a subset of the electrodes. Concentrator 164 and chambers 166, 168 may be defined by distinct compartments/passages, for example, as a serial array of compartments, as shown. Alternatively, these functional regions may be partially or completely overlapping, for example, with all provided by one chamber.

Concentrator 164 is configured to concentrate nucleic acids received from pre-processing chamber 154. Electrodes of concentrator 164 may be electrically biased positively, while allowing fluid to pass from fluid-handling portion 142, through the concentrator, and back to waste chamber 156 in fluid-handling portion 142. Accordingly, concentrator 164 may be connected fluidically to fluid-handling portion 142 at plural discrete sites (see FIGS. 11–17), allowing the concentrator to serve as a conduit. The conduit may allow transfer of a fluid volume (between two fluid-handling portion reservoirs) that is substantially larger than the fluid capacity of the concentrator. This processing step removes fluid, and may partially purify the nucleic acids by removing material that is positively charged, uncharged, or weakly negatively charged, among others.

In some embodiments, concentrator 164 is configured to perform nucleic acid preselection (see Section I). Such preselection may concentrate target nucleic acids in a volume that is small enough to perform additional processing, such as amplification, under control of thin-film electronic devices in the assay portion. Accordingly, preselection in concentrator 164 may facilitate transition of the sample from larger volumes in the fluid-handling portion to substantially smaller volumes in the assay portion, so that electronic processing of the target nucleic acid is enabled.

Amplification chamber 166 may be used to copy one or more target nucleic acid (or nucleic acids) from among the concentrated nucleic acids, using an amplification reaction to increase assay sensitivity. An amplification reaction generally includes any reaction that increases the total number of molecules of a target nucleic acid (or a region contained within the target species), generally resulting in enrichment of the target nucleic acid relative to total nucleic acids. Enzymes that replicate DNA, transcribe RNA from DNA, and/or perform templatedirected ligation of primers, may mediate the amplification reaction. Dependent upon the method and the enzymes used, amplification may involve thermal cycling (for example, polymerase chain reaction (PCR) or ligase chain reaction (LCR)) or may be isothermal (for example, strand-displacement amplification (SDA) or nucleic acid sequence-based amplification (NASBA)). With any of these methods, temperature control in chamber 166 may be determined by heaters, such as thin-film heaters included in circuitry 158. Nucleic acids may be labeled during amplification to facilitate detection, for example, by incorporation of labeled primers or nucleotides. Primers or nucleotides may be labeled with dyes, radioisotopes, or specific binding members, as described below in Section III and listed in Table 1. Alternatively, nucleic acids may be labeled in a separate processing step (for example, by terminal transferase, primer extension, affinity reagents, nucleic acid dyes, etc.), or prior to inputting the sample. Such separate labeling may be suitable, for example, when the amplification step is omitted because a sufficient amount of the target nucleic acid is included in the inputted sample.

Assay chamber 168 may perform a processing step that separates or distinguishes nucleic acids according to specific sequence, length, and/or presence of sequence motifs. In some embodiments, the assay chamber includes one or plural specific receptors for nucleic acids. Receptors may include any agent that specifically binds target nucleic acids. Exemplary receptors may include single-stranded nucleic acids, peptide nucleic acids, antibodies, chemical compounds, polymers, etc. The receptors may be disposed in an array, generally immobilized at defined positions, so that binding of a target nucleic acid to one of the receptors produces a detectable signal at a defined position(s) in the assay chamber. Accordingly, when amplification is used, amplified nucleic acids (targets) contact each of the receptors to test binding. A receptor array may be disposed proximate to electrodes that concentrate the targets electrically over receptors of the array, as described further below. In alternative embodiments, the assay chamber may separate target nucleic acids according to size, for example, using electrophoresis and/or chromatography. Alternatively, or in addition, the assay chamber may provide receptors that are not immobilized, such as molecular beacon probes and/or may provide a site for detection without receptors.

Optical interface 136 may measure sample processing at any suitable position of assay portion 144. For example, optical interface may include separate emitter-detector pairs for monitoring amplification of nucleic acids in amplification chamber 166, and for detecting binding and/or position of amplified nucleic acids after processing in assay chamber 168, as described above. Alternatively, or in addition, the optical interface may monitor fluid movement through chip fluid network 148.

FIG. 9 shows exemplary directions of fluid movement (reagents and/or sample) through fluid networks 146 and 148 during sample processing, indicated by thickened arrows, as shown at 170. Generally, fluid flows from reagent reservoirs 152 through sample input site 150 and pre-processing chamber(s) 154 to waste chamber(s) 156 and assay portion 144 (see below). Fluid that enters assay portion 144 from fluid-handling portion 142 may flow back to waste chamber(s) 156 or may be moved to other fluid compartments in the assay portion.

Figure 10:
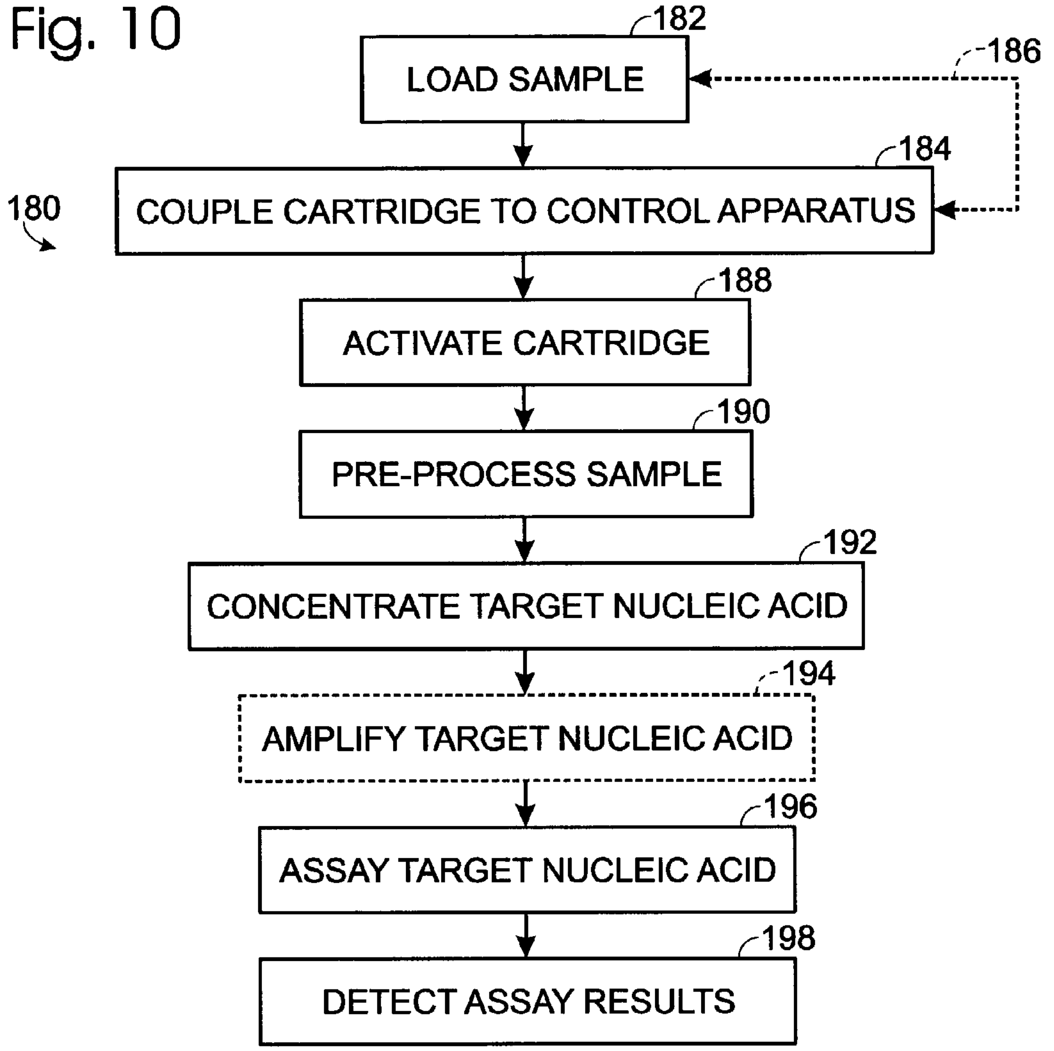
FIG. 10 is a flowchart illustrating an exemplary method of operation of the cartridge and control apparatus of FIG. 7, in accordance with an embodiment of the invention.

FIG. 10 shows a flowchart illustrating an exemplary method 180 for operation of cartridge 114 with control apparatus 112 to analyze target nucleic acid(s) in a sample. First, sample may be introduced (loaded) at sample input site 150 of cartridge 114, for example, by injection, as shown at 182. Next, the cartridge with its sample may be electrically coupled to control apparatus 114, as shown at 184, for example, by mating the cartridge with recess 116 for conductive contact. As indicated at 186, such loading and coupling may be performed in reverse order, that is, the sample may be introduced into the cartridge after it has been coupled to the control apparatus. The cartridge then may be activated to initiate processing, as shown at 188. The cartridge may be activated by input from a user through user interface 130, by coupling the cartridge to the control apparatus, by introducing a sample, and/or the like. After activation, the sample is pre-processed, as shown at 190. Pre-processing typically moves the sample to pre-processing chamber 154, and treats the sample to release and isolate nucleic acids, when necessary, as described further below. The isolated nucleic acids are moved to concentrator 164 in assay portion 144, generally by mechanically driven flow, and concentrated, as shown at 192. The concentrated nucleic acids may be amplified selectively, if needed, as shown at 194, with use of primers targeted to nucleic acids of interest. Next, the amplified nucleic acids may be assayed, for example, by contacting a receptor or receptor array with the amplified nucleic acids, as shown at 196. Assay results then may be detected optically and/or electrically, as shown at 198.

Figure 11:
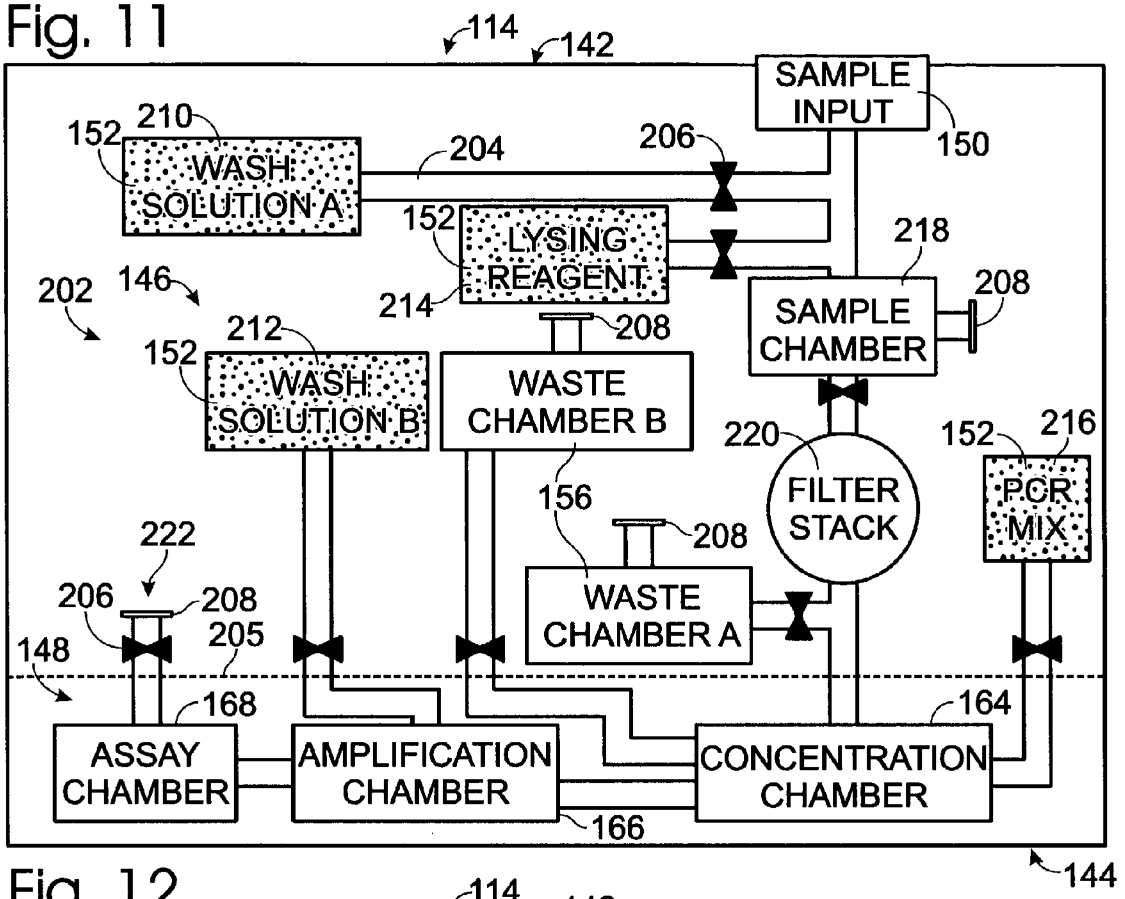
FIG. 11 is a more detailed schematic view of the cartridge of FIGS. 7 and 9, illustrating a fluid network for carrying out the method of FIG. 10.

FIG. 11 shows a more detailed representation of an exemplary self-contained fluid network 202 formed by interconnected fluid networks 146, 148 in fluid-handling portion 142 and assay portion 144 of cartridge 114, respectively. Chambers are represented as rectangles, or by a circle. Channels 204 that interconnect the chambers are represented by parallel lines. As shown, channels 204 fluidly connect fluid-handling portion 142 with assay portion 144 at positions where the channels cross an interface 205 between the two portions. Valves 206 are represented by solid "bowties" (closed valves) or by unfilled bowties (open valves; see below). Valves typically are electrically activated, and thus may be electrically coupled (not shown) to control apparatus 112. Alternatively, or in addition, valves may be mechanically operated by electrically activated valve actuators/regulators on control apparatus 112. Exemplary valves include solenoid valves and single use valves. Gas-selective vents 208 are represented by thin rectangles on terminated channels (see the vent on assay chamber 168, for example). Suitable valves and vents are described further in Section III.

FIG. 11 shows the cartridge ready to receive a sample and to be activated. Accordingly, the cartridge has been preloaded with reagents in reagent reservoirs 152, as shown by stippling to represent fluid. Preloaded reagent reservoirs 152 may carry wash solutions 210, 212 of suitable pH, buffering capacity, ionic strength, solvent composition, etc. One or more reservoirs 152 also may carry a lysing reagent 214, which may include, for example, a chaotropic agent, a buffer of high or low ionic strength, one or more ionic or nonionic detergents, an organic solvent(s), and/or the like. Furthermore, one or more reservoirs 152 may include an amplification mix, such as PCR mix 216, or any other mixture that includes one or more amplification reagents. In general, any nucleic acid(s) that selectively hybridizes to the nucleic acid(s) of interest may be an amplification reagent.

PCR mix 216 generally includes a suitable buffer, $Mg^{+2}$, specific primers for selective amplification of target nucleic acid(s), dNTPs, a heat stable polymerase, and/or the like. One or more primers and/or dNTPs may be labeled, for example with a dye or biotin, as described above. PCR mix 216 may be replaced with any other suitable amplification mixture, based on the amplification method implemented by the cartridge. Furthermore, in order to analyze RNA, PCR mix may include a reverse transcriptase enzyme. Alternatively, a separate reservoir may provide reagents to carry out synthesis of complementary DNA using the RNA as a template, generally prior to amplification.

Reagent reservoirs 152 may be configured to deliver fluid based on mechanically driven fluid flow. For example, reagent reservoirs 152 may be structured as collapsible bags, with a spring or other resilient structure exerting a positive pressure on each bag. Alternatively, reagent reservoirs 152 may be pressurized with a gas. Whatever the mechanism of pressurization, valve 206 may be operated to selectively control delivery of reagent from each reservoir. Section III describes additional exemplary mechanisms to produce mechanically driven fluid flow.

Cartridge 114 includes internal chambers for carrying out various functions. Internal chambers include waste chambers 156, in this case, two waste chambers, designated A and B. Waste chambers 156 receive fluids from reagent reservoirs 152 (and from sample input 150) and thus may include vents 208 to allow gas to be vented from the waste chambers. Internal chambers (passages) may include a sample chamber 218, a filter stack 220, and chip chambers 164, 166, 168. Sample chamber 218 and filter stack 220 are configured to receive and pre-process the sample, respectively, as described further below. Assay chamber 168 may be vented by a regulated vent 222, that is, a valve 206 that controls a vent 208. Some or all of the internal chambers and/or channels 204 may be primed with suitable fluid, for example, as part of cartridge manufacture. In particular, chambers/channels of assay portion 144 may be primed. Correspondingly, some chambers and/or channels may be unprimed prior to cartridge activation.

Figure 12:
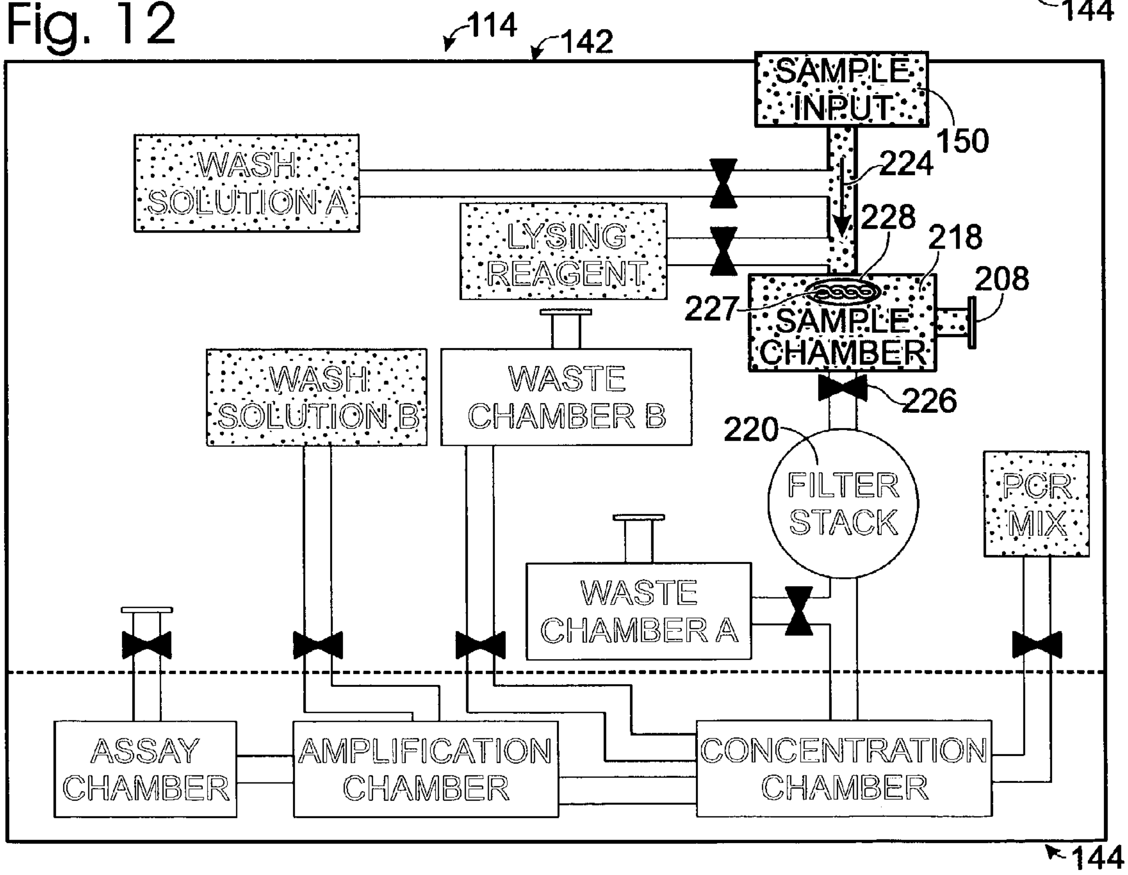
FIG. 12 is a schematic view emphasizing active regions of the cartridge of FIG. 11 during sample loading.

FIG. 12 shows active regions of fluid movement in cartridge 114 during sample loading. Here, and in FIGS. 13–16, heavy stippling indicates active regions, whereas light stippling indicates reagents or waste in reservoirs elsewhere in the cartridge. A sample, such as a liquid-based sample, is loaded at sample input site 150 and received by sample chamber 218, generally following a path indicated at 224. The volume of sample that may be loaded is limited here by a vent 208 on sample chamber 218, and by the capacity of sample chamber 218. Once sample chamber 218 is filled, vent 208 may provide a back pressure that limits introduction of additional sample. Alternatively, or in addition, an electrical or optical fluid sensor (not shown) may be placed within or around sample chamber 218 to signal when sample capacity is reached. A valve 226 downstream from sample chamber 218 may prevent the sample from flowing to filter stack 220 at this time, or the sample may be loaded directly onto the filter stack from sample input site 150, for example, by venting through waste chamber A.

The sample may be in any suitable form, for example, any of the samples described above in Section IV. However, the cartridge embodiment described here is configured to analyze nucleic acids 227, so samples generally contain nucleic acids, that is, DNA and/or RNA, or be suspected of carrying nucleic acid. Nucleic acids 227 may be carried in tissue or biological particles, may be in an extract from such, and/or may be partially or fully purified. Cells 228, viruses, and cell organelles are exemplary biological particles. The loaded sample volume may be any suitable volume, based on sample availability, ease of handling small volumes, target nucleic acid abundance in the sample, and/or cartridge capacity, etc.

Figure 13:
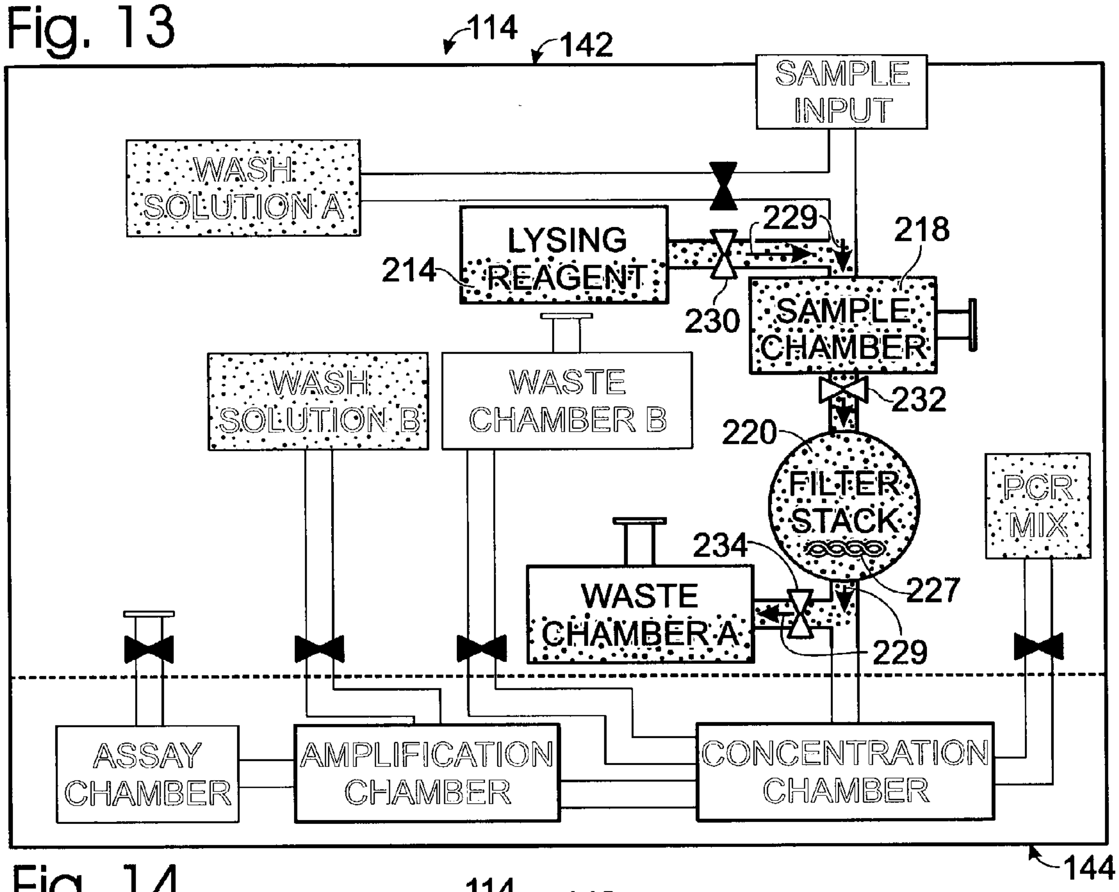
FIG. 13 is a schematic view emphasizing active regions of the cartridge of FIG. 11 during sample processing to isolate nucleic acids on a filter stack.

FIG. 13 shows active regions of fluid movement in cartridge 114 during sample pre-processing. Lysing reagent 214 may be introduced along path 229 by opening valves 230, 232, 234. The lysing reagent thus typically carries the sample with its nucleic acids 227 from sample chamber 218 to filter stack 220. Excess fluid may be carried to waste chamber A. The filter stack generally may be configured to perform nucleic acid isolation, that is, at least partial separation from sample waste material, through any or all of at least three functions: particle filtration, nucleic acid release from the sample, and retention of released nucleic acid. Waste material is defined here as any sample-derived component, complex, aggregate or particulate, among others, that does not correspond to the nucleic acid of interest. Exemplary waste material may include cell or viral debris, unbroken cells or virus particles, cell membranes, cytoplasmic components, soluble non-nucleic acid materials, insoluble non-nucleic acid materials, nucleic acids that are not of interest, and/or the like. Waste material also may be sample-derived fluid, removal of which concentrates the nucleic acids.

Filtration is any size selection process carried out by filters that mechanically retain cells, particles, debris and/or the like. Accordingly, the filter stack may localize sample particles (cells, viruses, etc.) for disrupting treatment and also may remove particulates that might interfere with downstream processing and/or fluid flow in cartridge fluid network 202. Suitable filters for this first function may include small-pore membranes, fiber filters, narrowed channels, and/or so on. One or more filters may be included in the filter stack. In some embodiments, the filter stack includes a series of filters with a decreasing exclusion limit within the series along the direction of fluid flow. Such a serial arrangement may reduce the rate at which filters become clogged with particles.

The sample retained on filter stack 220 may be subjected to a treatment that releases nucleic acids 227 from an unprocessed and/or less accessible form in the sample. Alternatively, or in addition, the releasing treatment may be carried out prior to sample retention on the filter stack. The treatment may alter the integrity of cell surface, nuclear, and/or mitochondrial membranes and/or may disaggregate subcellular structures, among others. Exemplary releasing treatments may include changes in pressure (for example, sonic or ultrasonic waves/pulses or a pressure drop produced by channel narrowing as in a French press); temperature shift (heating and/or cooling); electrical treatment, such as voltage pulses; chemical treatments, such as with detergent, chaotropic agents, organic solvents, high or low salt, etc.; projections within a fluid compartment (such as spikes or sharp edges); and/or the like. Here, nucleic acids 227 are shown after being freed from cells 228 that carried the nucleic acids.

Nucleic acid retention is generally implemented downstream of the filters. Nucleic acid retention may be implemented by a retention matrix that binds nucleic acids 227 reversibly. Suitable retention matrices for this second function may include beads, particles, and/or membranes, among others. Exemplary retention matrices may include positively charged resins (ion exchange resins), activated silica, and/or the like. Once nucleic acids 227 are retained, additional lysing reagent or a wash solution may be moved past the retained nucleic acid 227 to wash away unretained contaminants.

Figure 14:
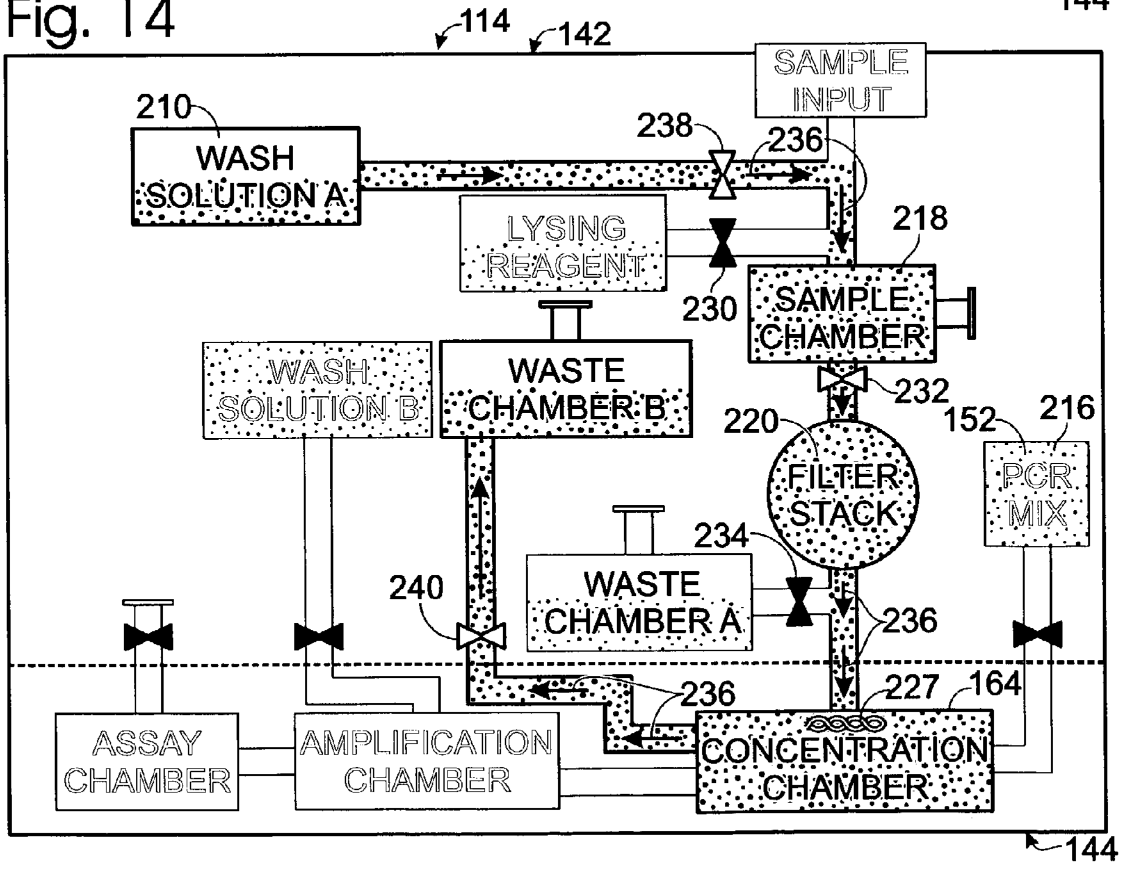
FIG. 14 is a schematic view emphasizing active regions of the cartridge of FIG. 11 during release of the nucleic acids from the filter stack and concentration of the released nucleic acids in an assay portion of the cartridge.

FIG. 14 shows active regions of fluid movement in cartridge 114 during release of nucleic acids 227 from filter stack 220 and concentration of the released nucleic acids 227 in concentration chamber 164 of assay portion 144. Fluid flows from wash solution A, shown at 210, to a distinct waste chamber, waste chamber B, along fluid path 236, through sample chamber 218 and filter stack 220. To initiate flow along path 236, valves 230 and 234 are closed, valve 232 remains open, and valves 238 and 240 are opened. Wash solution A may be configured to release nucleic acids 227 that were retained in filter stack 220 (see FIG. 7). Accordingly, wash solution A may be formulated based on the mechanism by which nucleic acids 227 are retained by the retention matrix in the filter stack. Wash solutions to release retained nucleic acid may alter the pH, ionic strength, and/or dielectric constant of the fluid, among others. Exemplary wash solutions may include a high or low pH, a high or low ionic strength, an organic solvent, and/or so on. Pre-processing may provide a first-step concentration and purification of nucleic acids from the sample.

Released nucleic acids 227 may be concentrated (and purified) further at concentration chamber 164. Concentration chamber 164 typically is formed in assay portion 144, and includes one, or typically plural electrodes. At least one of the electrodes may be electrically biased (positively) before or as the released nucleic acids enter concentration chamber 164. As a result, nucleic acids 227 that flow through concentration chamber 164 may be attracted to, and retained by, the positively biased electrode(s). Bulk fluid that carries nucleic acids 227, and additional wash solution A, may be carried on to waste chamber B. Accordingly, nucleic acids 227 may be concentrated, and may be purified further by retention in concentration chamber 164. This concentration of nucleic acids 227 may allow assay portion 144 to have fluid compartments that are very small in volume, for example, compartments, in which processing occurs, having a fluid capacity of less than about one microliter. Further aspects of electrode structure, number, disposition, and coating are described below.

In some embodiments, concentration chamber 164 is configured as a preselection chamber, such as preselection chamber 64 of FIGS. 3–6. Accordingly, concentration chamber 164 may be used to concentrate and enrich a pre-processed sample for a target nucleic acid(s) of interest, so that the preselected target can be further processed more efficiently, as described below.

Figure 15:
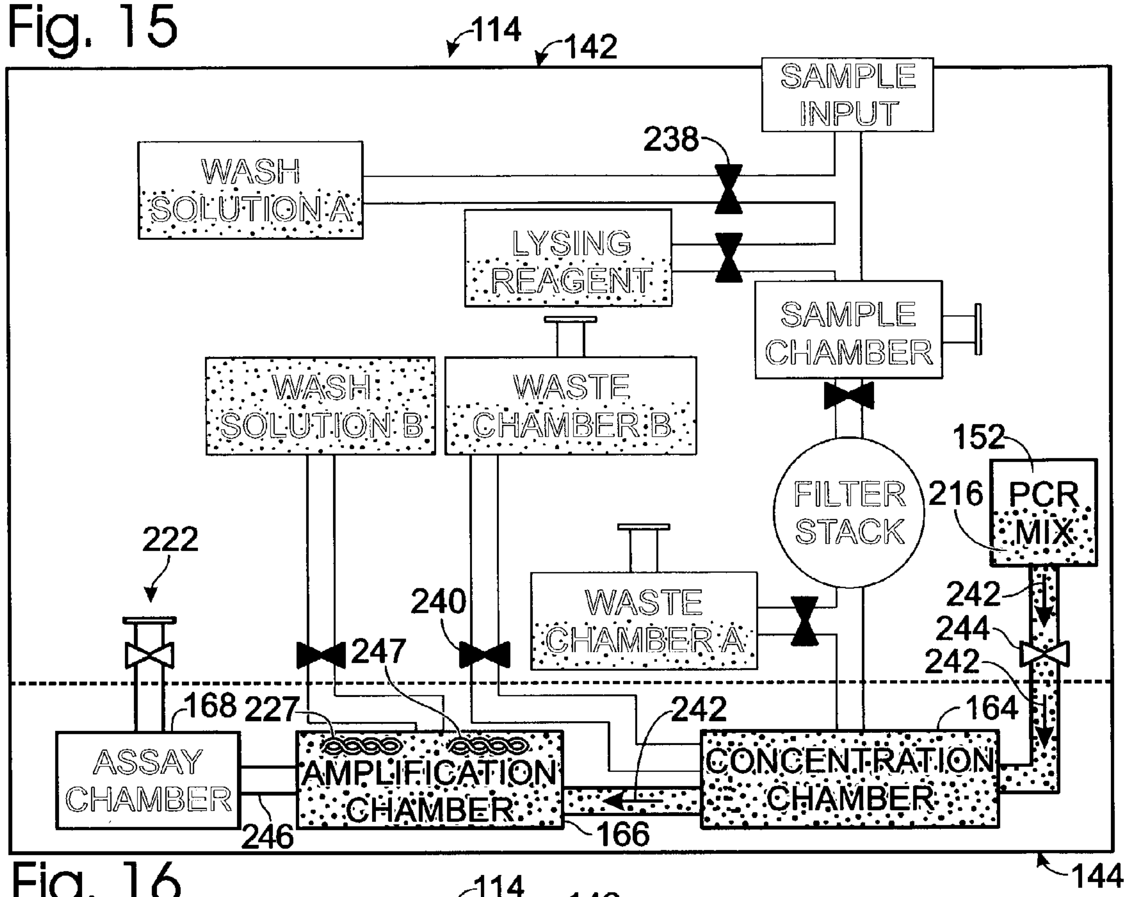
FIG. 15 is a schematic view emphasizing active regions of the cartridge of FIG. 11 during equilibration of the concentrated nucleic acids with amplification reagents and transfer to an amplification chamber on the assay portion.

FIG. 15 shows active regions of fluid movement in cartridge 114 during transfer of concentrated nucleic acids to amplification chamber 166 of assay portion 144. As shown, typically fluid flows from a chamber 152, holding PCR mix 216, to amplification chamber 166 along fluid path 242. To activate flow along path 242, valve 238 and 240 are closed, and valve 244 and vent-valve 222 are opened, as the retaining positive bias is removed from the electrode(s) in concentration chamber 164. PCR mix 216 may carry nucleic acids 227 by fluid flow. Alternatively, a positive bias may be imparted to electrodes in amplification chamber 166 (see below) to electrophoretically transfer nucleic acids 227 to amplification chamber 166, which is preloaded with PCR mix 216. In either case, flow of excess fluid out of amplification chamber 166 and into assay chamber 168 may be restricted, for example, by an electrical or optical sensor (not shown) that monitors fluid level in connecting channel 246 and signals timely closing of vent-valve 222. In some embodiments, concentration chamber 164 first may be equilibrated with PCR mix 216 prior to moving nucleic acids 227 to amplification chamber 166. For example, PCR mix 216 may be directed through an opened valve 240 to waste chamber B, before removing the retaining positive bias in concentration chamber 164 and opening vent-valve 222. Nucleic acids 227 positioned in amplification chamber 166 may be amplified, for example, by isothermal incubation or thermal cycling, to selectively increase the amount of nucleic-acid targets (or target regions) of interest 247 among nucleic acids 227, or, in some cases, may remain unamplified.

Figure 16:
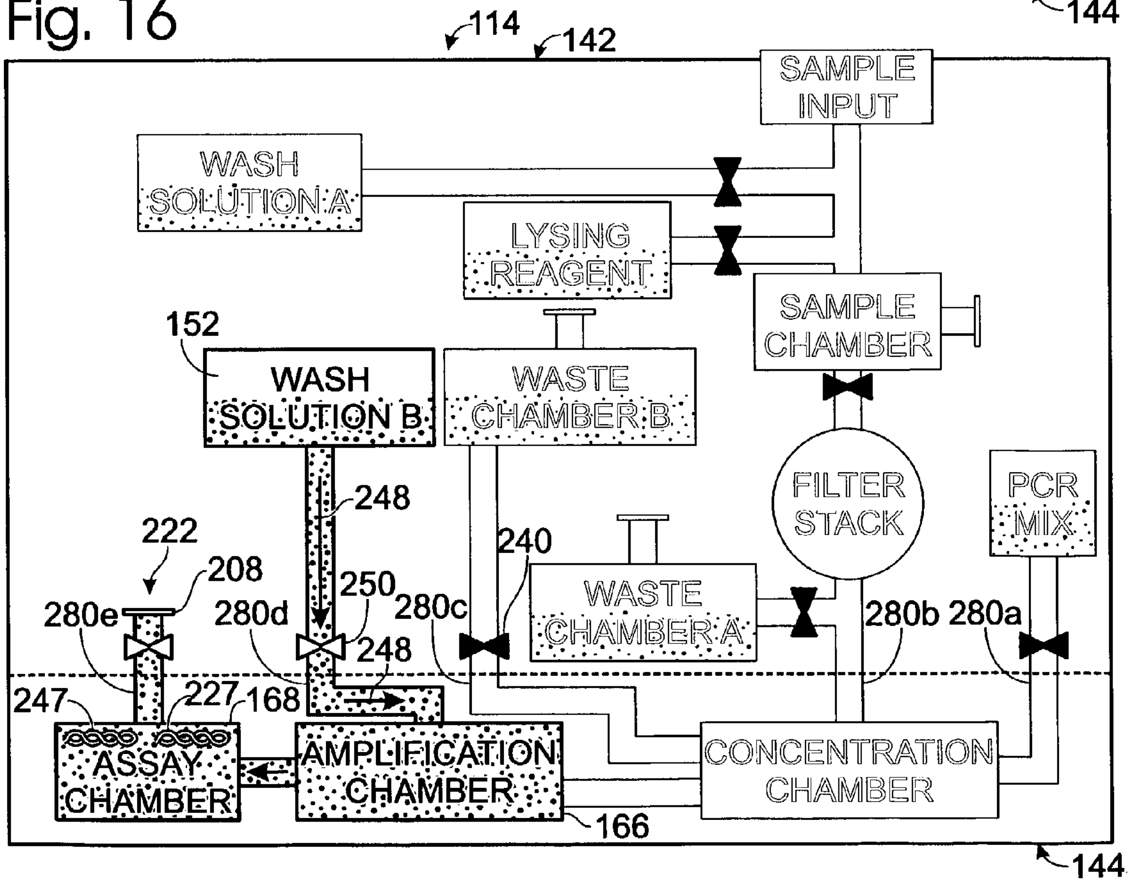
FIG. 16 is a schematic view emphasizing active regions of the cartridge of FIG. 11 during transfer of the nucleic acids, after selective amplification, to an assay chamber on the assay portion.

FIG. 16 shows active regions of fluid movement in cartridge 114 during transfer of amplified nucleic acids 247 to assay chamber 168 of assay portion 144. Fluid flows along fluid path 248 from a chamber 152 that holds wash solution B to assay chamber 168. Fluid path 248 may be activated by opening valve 250 and vent-valve 222. Overfilling assay chamber 168 may be restricted, for example, by vent 208 on vent-valve 222, or by a sensor that monitors fluid position and signals the closing of valve 250, among others. As described above, nucleic acids 227 and amplified target nucleic acids 247 may be transferred by fluid flow and/or electrophoretically using electrodes disposed in assay chamber 168 (see below). In some embodiments, amplification chamber 166 first may be equilibrated with wash solution B by closing vent-valve 222 and opening valves 240, 250, thus directing wash solution B through amplification chamber 166, concentration chamber 164, and into waste chamber B. Alternatively, or in addition, amplified nucleic acid(s) 247 may be transferred electrophoretically to an assay chamber 168 preloaded with assay solution.

Amplified target nucleic acid(s) 247 (and isolated nucleic acids 227) may be assayed in assay chamber 168. For example, assay chamber 168 may include one or more positioned receptors (a positional array) for nucleic acid identification and/or quantification, as described in Section 111. Hybridization of amplified nucleic acids 247 to receptors may be assisted by electrodes positioned near to the receptors in assay chamber 168. The electrodes may be biased positively in a sequential manner to direct the amplified nucleic acids to individual members (or subgroups) of the array. After electrophoretically moving amplified target nucleic acid(s) 247 to many or all positions of the array, to allow specific binding or hybridization, unbound or unhybridized nucleic acid(s) may be removed electrophoretically and/or by fluid flow (not shown here).

Figure 17:
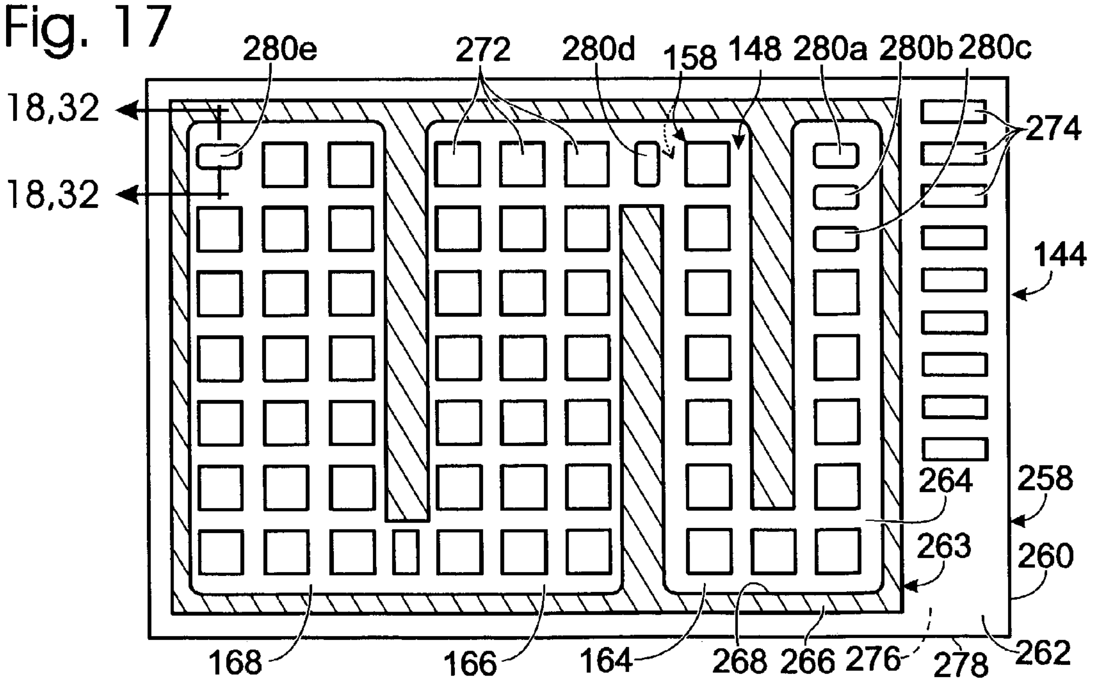
FIG. 17 is a plan view of the assay portion included in the cartridge of FIGS. 7 and 11, viewed from external the cartridge and showing selected aspects of the assay portion, in accordance with an embodiment of the invention.
Figure 18:
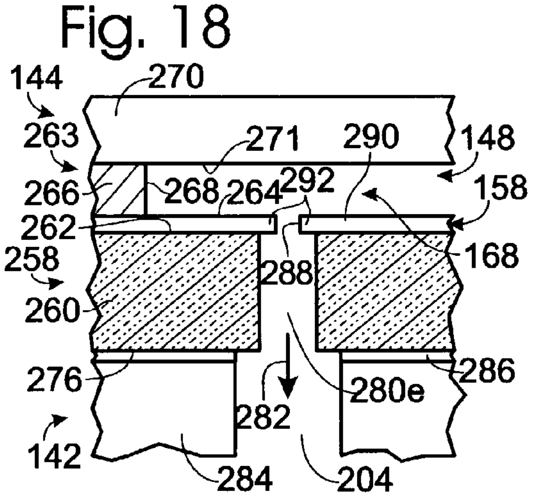
FIG. 18 is a fragmentary sectional view of the assay portion of FIG. 17, viewed generally along line 18—18 of FIG. 17, and shown attached to the fluid-handling portion of the cartridge of FIGS. 7 and 11, in accordance with an embodiment of the invention.

FIGS. 17 and 18 show selected aspects of assay portion 144, viewed in plan from external cartridge 114 and in cross-section, respectively. Assay portion 144 includes a substrate portion 258. Substrate portion 258 at least partially defines fluid compartments of the assay portion. The substrate portion may include a substrate 260. The substrate portion also may include electronic circuitry 158 and/or thin-film layers formed on the substrate and disposed near a surface 262 of the substrate. Thin-film electronic devices of the circuitry and fluid compartments of network 148 each may be disposed near a common surface of the substrate so that the electronic devices are closely apposed to, and/or in fluid contact with, regions of the fluid network. Thus, the thin-film devices may be configured to modify and/or sense a property of fluid (or sample/analyte) in fluid network 148. An exemplary material for substrate 260 is silicon, typically monocrystalline silicon. Other suitable substrate materials and properties are described below in Section III.

Fluid network 148 or a fluidically connected fluid space of one or more fluid compartments may be cooperatively defined near a surface 262 of the substrate using substrate portion 258 and a fluid barrier 263. The fluid space may determine total fluid capacity for holding fluid between the substrate portion and the fluid barrier. The term "cooperatively defined" means that the fluid space, or a fluid compartment thereof, is disposed substantially (or completely) between substrate portion 258 and fluid barrier 263. Fluid barrier 263 may be any structure that prevents substantial escape or exit of fluid out of the device, through the barrier, from fluid network 148, or a compartment thereof. Preventing substantial exit of fluid from the cartridge means that drops, droplets, or a stream of fluid does not leave the device through the fluid barrier. Accordingly, the fluid barrier may be free of openings that fluidically connect fluid network 148 to regions exterior to the device. The fluid barrier also may fluidically seal a perimeter defined at the junction between the fluid barrier and the substrate portion to prevent substantial exit of fluid from the cartridge at the junction. Typically, the fluid barrier also restricts evaporative loss from fluid network 148.

Fluid network 148 may be formed as follows. Surface 262 of substrate 260 and/or circuitry 158 may define a base wall 264 of fluid network 148. A patterned channel layer 266 may be disposed over surface 262 and base wall 264 to define side walls 268. Channel layer 266 may be formed from any suitable material, including, but not limited to, a negative or positive photoresist (such as SU-8 or PLP), a polyimide, a dry film (such as DuPont Riston), and/or a glass. Methods for patterning channel layer 266 may include photolithography, micromachining, molding, stamping, laser etching, and/or the like. A cover 270 may be disposed on channel layer 266, and spaced from base 264, to seal a top region of fluid network 148 that is spaced from electronic circuitry 158 (see FIG. 18). Cover 270 may be a component separate from channel layer 266, such as a layer that is bonded or otherwise attached to channel layer 266, or may be formed integrally with channel layer 266. In either case, fluid barrier 263 may include an opposing wall 271 that is sealed against fluid movement and escape from the cartridge. Cover 270 may be transparent, for example, glass or clear plastic, when assays are detected optically through the cover. Alternatively, cover 270 may be optically opaque, for example, when assays are detected electrically. Fluid network 148 may include spatially distinct chambers 164, 166, 168, as described above, to carry out distinct processes, and/or distinct processes may be carried out in a shared fluid compartment.

At least a thin-film portion of circuitry 158 may be formed above, and carried by, surface 262 of substrate 260. The circuitry typically includes thin-film layers that at least partially define one or more electronic circuit. The circuitry may include electrodes 272 that contact fluid in fluid network 148. Electrodes and other thin-film devices (see Section III) may be electrically coupled to electrical contact pads 274 (see FIG. 17), generally through semiconductor circuitry (including signal processing circuitry) formed on the substrate, that is, fabricated on and/or below surface 262. A given number of contact pads 274 may control a substantially greater number of electrodes and/or other thin-film devices. In preferred embodiments, contact pads 274 are electrically coupled to contacts 118, such as with a flexible circuit.

Electrodes 272 may have any suitable composition, distribution, and coating. Suitable materials for electrodes 272 are conductive materials, such as metals, metal alloys, or metal derivatives. Exemplary electrode materials include, gold, platinum, copper, aluminum, titanium, tungsten, metal silicides, and/or the like. Circuitry 158 may include electrodes at one or plural sites along base 264 of fluid network 148. For example, as shown here, electrodes may be arrayed as plural discrete units, either in single file along a channel/chamber, as in concentrator 164, and/or in a two-dimensional array, as in chambers 166, 168. Alternatively, or in addition, electrodes 272 may be elongate or have any other suitable shape or shapes. Each electrode 272 may be biased electrically on individual basis, either positively or negatively, so that nucleic acids are attracted to, or repelled from, the electrode, or the electrode may be electrically unbiased. Electrical biasing may be carried out in any suitable spatially and time-regulated manner by control apparatus 112 and/or cartridge 114, based on desired retention and/or directed movement of nucleic acids. Electrodes 272 may be coated with a permeation layer to allow access of fluid and ions to the electrode in the fluid compartment, but to exclude larger molecules (such as nucleic acids) from direct contact with the electrodes. Such direct contact may chemically damage the nucleic acids. Suitable electrode coatings may include hydrogels and/or sol-gels, among others, and may be applied by any suitable method, such as sputtering, spin-coating, etc. Exemplary materials for coatings may include polyacrylamides, agaroses, and/or synthetic polymers, among others.

Assay portion 144 is fluidically connected to fluid-handling portion 142. Any suitable interface passage (or a single passage) may be used for this connection to join fluid networks 146, 148 of the cartridge. Such fluid connection may allow fluid to be routed in relation to a fluid compartment, that is, to and/or from the fluid compartment.

Fluid networks 146, 148 may be separated spatially by substrate 260 and/or fluid barrier 263. When separated by substrate 260, interface passages may extend through substrate 260, generally between surface 262 of substrate 260 and opposing surface 276, to join the fluid networks. Interface passages may be described as feed structures to define paths for fluid movement. Alternatively, or in addition, one or more interface channels may extend around an edge 278 (FIG. 17) of substrate 260 to connect to fluid network 146 (FIGS. 11–16). For example, interface channels may extend through channel layer 266 and/or cover 270, but sealed against substantial exit of fluid from the cartridge. In alternative embodiments, fluid networks 146, 148 may be separated spatially by fluid barrier 263 rather than substrate 260, with some or all interface channels again extending through fluid barrier 263 to connect fluidly to fluid network 146.

In the depicted embodiment, interface passages, labeled 280*a* through 280*e*, extend through substrate 260 between opposing surfaces of the substrate (see FIGS. 16–18). An interface passage 280 may fluidly connect any fluid compartment of the fluid-handling portion to a fluid compartment of fluid network 148, generally by directly linking to fluid conduits or chambers of the two portions. For example, an interface passage 280 may connect a reagent reservoir 152 to a chamber (164–168) of assay portion 144, a chamber of the assay portion to a waste chamber, pre-processing chamber 220 to a chamber of the assay portion, two or more chambers of the assay portion to each other (not shown), a sample input site 150 directly to a chamber of the assay portion (also not shown), and/or a chamber of the assay portion to a valve and/or vent (such as valve-vent 222), among others. Each individual compartment of the assay portion may connect directly to any suitable number of interface passages 280. Here, concentration chamber 164 has three, 280*a*–280*c*, and amplification chamber 166 and assay chamber 168 each have one, 280*d* and 280*e*, respectively.

FIG. 18 shows how interface passage 280*e* fluidly connects assay portion 144 to fluid-handling portion 142. Interface passage 280*e* is configured to carry fluid along fluid path 282, from assay chamber 168 to valve-vent 222 (see FIG. 16). The interface passage may carry fluid to a channel (or channels) 204 of fluid-handling portion 142. Each channel 204 may be connected to an interface passage 280 through a fluid manifold 284 that directs fluid to one or plural channels 204 in fluid-handling portion 142, and to one or plural fluid compartments in assay portion 144. Accordingly, assay portion 144 may be attached fixedly to fluid manifold 284, for example, by using an adhesive 286.

An interface passage may have a diameter that varies along its length (measured generally parallel to direction of fluid flow). For example, the diameter of interface passage 280*e* may be smaller adjacent surface 262 of substrate 260, at an end region of the channel, than within an intermediate region defined by substrate 260, to form an opening 288 for routing fluid. The opening routes fluid by directing fluid to and/or from a fluid compartment. Opening 288 typically adjoins a fluid compartment. The fluid compartment is defined at least partially by the fluid barrier and may be configured so that fluid cannot exit the microfluidic device locally from the compartment, that is, directly out through the fluid barrier. The fluid compartment may be defined cooperatively between the substrate portion and the fluid barrier. The opening may include a perimeter region that forms an overhang (or shelf) 292 in which film layers 290 do not contact substrate 260. Opening 288 may have any suitable diameter, or a diameter of about 1 μm to 100 μm. The opening or hole may provide more restricted fluid flow than the substrate-defined region of the interface passage alone. Opening 288 may be defined by an opening formed in one or more film layers 290 formed on surface 262 of substrate 260. Film layers 290 typically are thin, that is, substantially thinner than the thickness of substrate 260, and may have a thickness and/or functional role as described in Section III.

FIGS. 19–25 show stepwise formation of interface passage 280*e*, opening 288, and assay chamber 168, in assay portion 144, using an exemplary method for fabrication of the assay portion. Suitable film deposition and patterning steps are described in U.S. Pat. No. 6,000,787 to Weber et al. and U.S. Pat. No. 6,336,714 to Kawamura et al., which are commonly owned and incorporated herein by reference. Here, patterning generally refers to the process of patterned deposition of a film layer after, for example, selective exposure of regions of the film layer to light.

Figure 19:
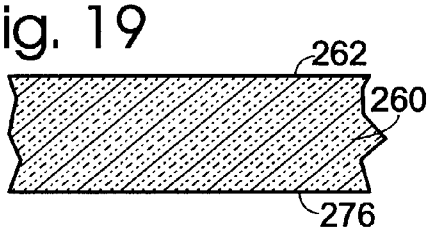
FIGS. 19–25 are fragmentary sectional views of a substrate during its modification to produce the assay portion shown in FIG. 18.

FIG. 19 shows a suitable starting material for the assay portion: a substantially planar substrate 260, with opposing surfaces 262, 276. The method described here may be carried out with a silicon substrate that is thin, for example, having a thickness of about 0.1 to 2 mm, or 0.2 to 1 mm. The substrate may be modified at surface 262, during and/or after, but typically before addition of film layers 290, to include n- and p-doped regions that form transistors, FETS, bipolar devices, and/or other semiconductor electronic devices (not shown).

Figure 20:
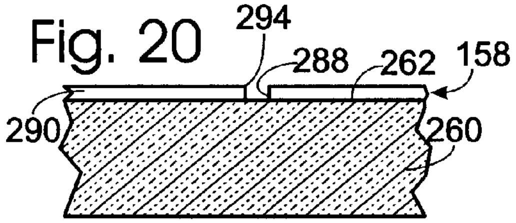

FIG. 20 shows the assay portion after application and patterning of film layers 290 on surface 262 of substrate 260. Film layers 290 may include any suitable films used to form and/or protect conductive portions of circuitry 158. Film layers may be formed of conductive material (for example, to form electrodes and conductive connections between devices), semiconductive material (for example, to form transistors using n- and p-doped material), and/or insulating material (for example, passivation layers). Film layers may be applied and patterned by conventional methods. At least one of film layers 290 may be patterned to define perimeter 294 of opening 288.

Figure 21:
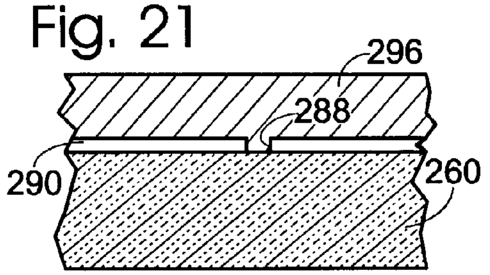

FIG. 21 shows the assay portion after unpatterned channel layer 296 has been disposed on film layers 290 and opening 288. Channel layer 296 may be applied at an appropriate thickness, typically a thickness of about 1–200 μm, more typically 2–100 μm, or even 5–50 μm. Exemplary materials for channel layer 296 (and the fluid barrier) are described above.

Figure 22:
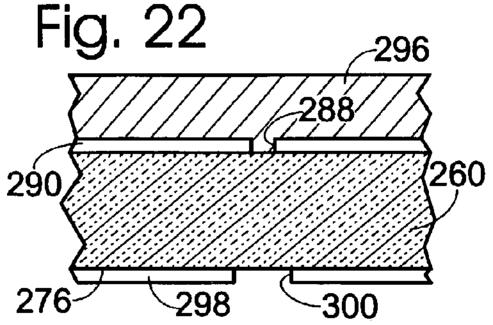

FIG. 22 shows the assay portion after an etch mask 298 has been added to opposing surface 276 of substrate 260. The etch mask may be applied as a layer of appropriate thickness, and selectively removed at a localized region (or regions) to define opening 300. Opening 300 may have any suitable diameter, but typically has a diameter greater than the diameter of opening 288. Opening 300 may be disposed opposite opening 288 so that a projection of opening 300 onto film layers 290 forms a corresponding channel or through-hole 301 in the substrate that may encompass opening 288 circumferentially.

Figure 23:
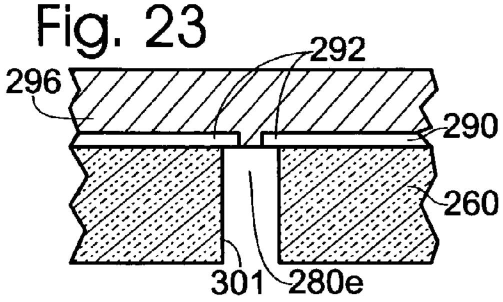

FIG. 23 shows the assay portion after formation of the substrate region of interface passage 280*e*, and after removal of etch mask 298. Substrate 260 may be etched generally orthogonally from surface 276 along a volume defined by aperture 300 (see FIG. 22) to produce channel 301. Any suitable etching procedure may be used to form the substrate portion of interface passage 280*e*. However, deep-reactive ion etching (DRIE) typically is used. One or more layers of film layers 290 may act as an etch stop, so that overhang region 292 is formed. After etching, the mask may be stripped from opposing surface 276 or left on the surface.

Figure 24:
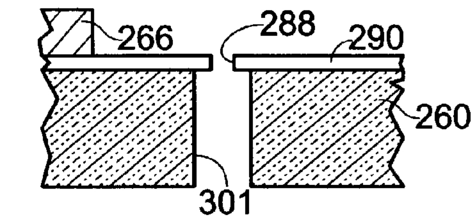

FIG. 24 shows the assay portion after regions of the unpatterned channel layer 296 have been selectively removed to form patterned channel layer 266. Selective removal may be carried out by any appropriate process, for example, photo-patterning layer 296 followed by development of the photo-patterned layer, or laser ablation.

Figure 25:
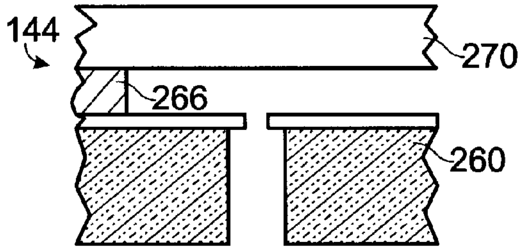

FIG. 25 shows the completed assay portion 144 after attachment of cover 270, but prior to affixing the assay portion to fluid-handling portion 142 through manifold 284. Cover 270 may be attached to fluid barrier 266 by any suitable method, such as with an adhesive, heat and pressure application, anodic bonding, sonic welding, and/or conventional methods.

Figure 26:
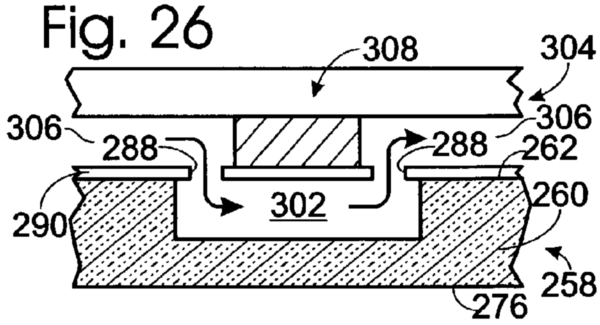
FIG. 26 is a schematic view of a channel that fluidly connects two fluid compartments formed adjacent a substrate surface, in which the channel enters and exits the substrate at the surface without communicating with the opposing surface of the substrate, in accordance with an embodiment of the invention.

FIG. 26 shows a somewhat schematic representation of an intra-chip passage 302 formed in assay portion 304. Intra-chip passage 302 may enter and exit substrate 260 from surface 262 through openings 288, without extending to opposing surface 276. Therefore, intra-chip passage 302 is distinct from interface passages 280 that extend between cartridge portions 142, 144. Intra-chip passage(s) 302 may be used to route fluid between chambers 306 defined cooperatively by substrate portion 258 and fluid barrier 308. Alternatively, or in addition, intra-chip passages may be used to mix fluid (see below), to perform a reaction or assay, and/or the like.

Figure 27:
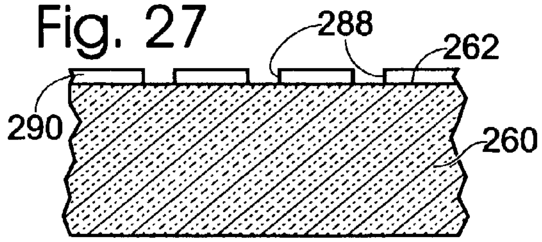
FIGS. 27–29 are fragmentary sectional views of a substrate during its modification to produce the channel of FIG. 26.
Figure 28:
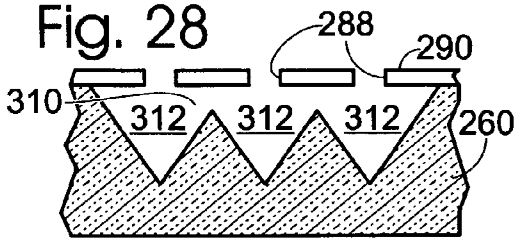
Figure 29:
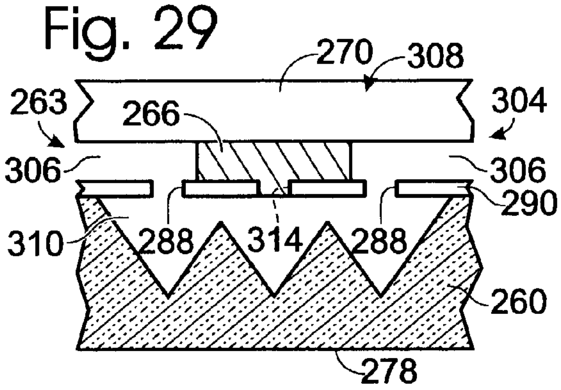

FIGS. 27–29 show stepwise formation of intra-chip passage 302 in assay portion 304 using an exemplary method. Materials and process steps are generally as described above for FIGS. 18–25. FIG. 27 shows a stage of fabrication after film layers 290 have been formed on surface 262 of substrate 260 and patterned to form plural openings 288. FIG. 28 shows the assay portion after anisotropic etching of substrate 260 under openings 288 to form a substrate recess or trough 310. Alternatively, trough 310 may be formed by isotropic etching. In either case, etchant may access substrate 260 through openings 288 to undercut film layers 290, thus joining local recesses 312, disposed under each opening 288, to form trough 310. Accordingly, openings 288 typically are spaced closely enough to allow recesses 312 to be connected fluidically during etching of substrate 260. FIG. 29 shows assay portion 304 after formation of chambers 306 using fluid barrier 308. Here, fluid barrier 308 includes channel layer 266, to define chamber side walls, and cover 270, to seal the top of chambers 306. One or more of openings 288 defined by film layers 290 and used to form trough 310 may be blocked by channel layer 266. For example, the central opening here has been sealed by channel layer 266, as shown at 314.

Figure 30:
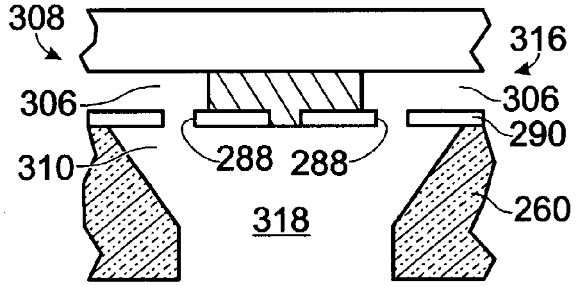
FIG. 30 is a fragmentary sectional view of a modified version of the channel of FIG. 23.

FIG. 30 shows an assay portion 316 having a manifold channel 318. Manifold channel 318 is a trans-substrate passage that connects fluidically to two or more openings 288 in thin films 290. Here, openings 288 fluidically connect manifold channel 318 to two chambers 306. However, manifold channel 318 may fluidically connect to any suitable number of compartments in the fluid network of the assay portion. Manifold channel 318 may be used to receive (or deliver) fluid from (or to) fluid-handling portion 142, for example, to deliver (or receive) fluid to (or from) one or both of chambers 306. Manifold channel 318 also may be used to direct fluid between chambers 306, as indicated in FIG. 26. An exemplary method for forming manifold channel 318 follows the procedure outlined in FIGS. 21–25, after formation of trough 310 in FIG. 28.

Figure 31:
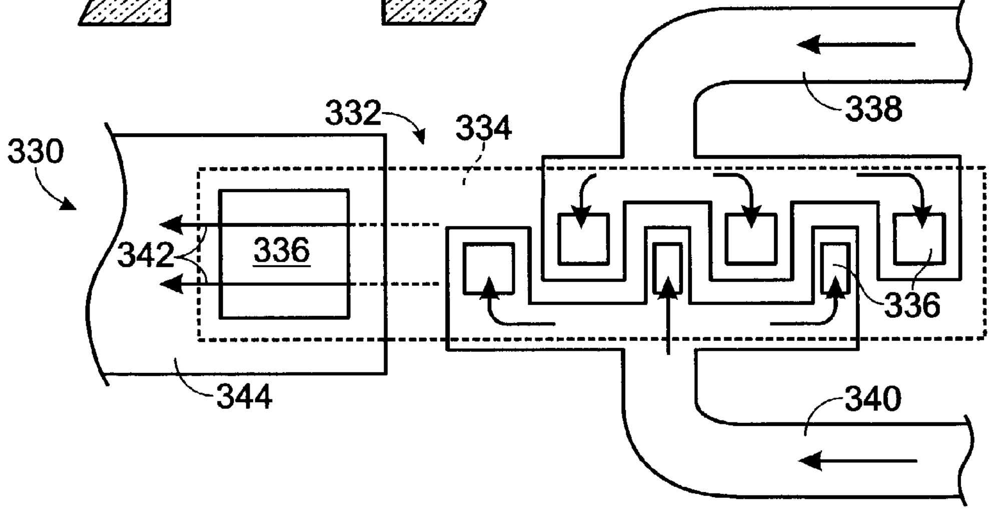
FIG. 31 is a plan view of an embodiment of a mixing chamber that may be formed in an assay portion using a variation of the substrate modification illustrated in FIGS. 27–29.

FIG. 31 shows a top plan, fragmentary view of an assay portion 330 that includes a mixing chamber 332. Mixing chamber 332 has a trough 334 similar to trough 310 of FIG. 28, formed under film layers at plural openings 336 (six inlet openings and one outlet opening are shown here). Trough 334 is fed from the fluid network of assay portion 330 by plural inlet channels 338, 340, which carry fluid into inlet openings along paths indicated by the arrows. Each channel may direct fluid, generally distinct fluids, into trough 334 using an interleaved geometry along the trough to allow mixing of the fluids from the plural channels within the trough. Mixed fluid exits trough 334, shown at 342, at an outlet opening 336 to direct fluid back into an outlet channel 344 of the fluid network of assay portion 330. In alternative embodiments, any suitable number of inlet and outlet channels may be connected to mixing chamber 332 through any suitable number of openings 336.

Figure 32:
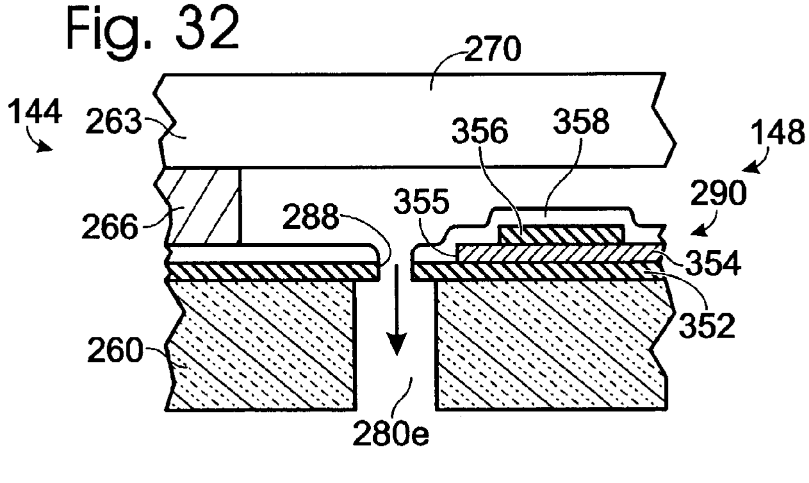
FIG. 32 is a more detailed view of selected aspects of FIG. 18, illustrating disposition of selected thin-film layers relative to an assay chamber and a substrate-defined channel, in accordance with an embodiment of the invention.

FIG. 32 shows selected portions of assay portion 144, particularly film layers 290, in more detail. Exemplary thin films may include a field oxide (FOX) layer 352, formed from substrate 260, and a phosho-silicate glass (PSG) layer 354 disposed over FOX layer 352. FOX layer 352 may provide a thermal barrier to thermally insulate heating effects. PSG layer 354 may be pulled back from opening 288, shown at 355, to avoid fluid contact with the PSG layer, which may have corrosive effects. Accordingly, PSG layer 354 defines a protected opening with a larger diameter than fluid-contacting opening 288. The thin films also may include a resistor layer 356, formed of any suitable resistive material, such as tantalum aluminum (TaAl). Current passes through the resistor layer 356 from connected conductors, formed of any appropriate conductive material, such as aluminum or an aluminum alloy (not shown). The resistor layer produces heat, which may be insulated from substrate 260 by FOX layer 352, among others. One or more passivation layers 358 may cover these thin films. Suitable materials for a passivation layer may include silicon nitride ($Si_3N_4$) or silicon carbide (SiC), among others. Additional electronic circuitry features, such as electrodes, transistors, and diodes, which may be disposed above and/or below the surface of the substrate, are not shown here.

III. Microfluidic Systems

Microfluidic systems are provided for sample manipulation and/or analysis. Microfluidic systems generally include devices and methods for receiving, manipulating, and analyzing samples in very small volumes of fluid (liquid and/or gas). The small volumes are carried by one or more fluid passages, at least one of which typically has a cross-sectional dimension or depth of between about 0.1 to 500 μm, or, more typically, less than about 100 μm or 50 μm. Microfluidic devices may have any suitable total fluid capacity. Accordingly, fluid at one or more regions within microfluidic devices may exhibit laminar flow with minimal turbulence, generally characterized by a low Reynolds number.

Fluid compartments may be fluidically connected within a microfluidic device. Fluidically connected or fluidically coupled generally means that a path exists within the device for fluid communication between the compartments. The path may be open at all times or be controlled by valves that open and close (see below).

Various fluid compartments may carry and/or hold fluid within a microfluidic device and are enclosed by the device. Compartments that carry fluid are passages. Passages may include any defined path or conduit for routing fluid movement within a microfluidic device, such as channels, processing chambers, apertures, or surfaces (for example, hydrophilic, charged, etc.), among others. Compartments that hold fluid for delivery to, or receipt from, passages are termed chambers or reservoirs. In many cases, chambers and reservoirs are also passages, allowing fluid to flow through the chambers or reservoirs. Fluid compartments within a microfluidic device that are fluidically connected form a fluid network or fluid space, which may be branched or unbranched. A microfluidic device, as described herein, may include a single fluidically connected fluid network or plural separate, unconnected fluid networks. With plural separate fluid networks, the device may be configured to receive and manipulate plural samples, at the same time and/or sequentially.

Chambers may be classified broadly as terminal and intermediate chambers. Terminal chambers generally may define as a starting point or endpoint for fluid movement within a fluid network. Such chambers may interface with the external environment, for example, receiving reagents during device manufacture or preparation, or may receive fluid only from fluid pathways within the microfluidic device. Exemplary terminal chambers may act as reservoirs that receive and/or store processed sample, reagents, and/or waste. Terminal chambers may be loaded with fluid before and/or during sample analysis. Intermediate chambers may have an intermediate position within a fluid network and thus may act as passages for processing, reaction, measurement, mixing, etc. during sample analysis.

Microfluidic devices may include one or more pumps to push and/or pull fluid or fluid components through fluid networks. Each pump may be a mechanically driven (pressure-mediated) pump or an electrokinetic pump, among others. Mechanically driven pumps may act by positive pressure to push fluid through the network. The pressure may be provided by a spring, pressurized gas (provided internally or external to the system), a motor, a syringe pump, a pneumatic pump, a peristaltic pump, and/or the like. Alternatively, or in addition, a pressure-driven pump may act by negative pressure, that is, by pulling fluid towards a region of decreased pressure. Electrokinetic or electrically driven pumps may use an electric field to promote flow of fluid and/or fluid components by electrophoresis, electroosmosis, electrocapillarity, and/or the like. In some embodiments, pumps may be micropumps fabricated by micromachining, for example, diaphragm-based pumps with piezoelectric-powered movement, among others.

Valves may be included in microfluidic devices described herein. A valve generally includes any mechanism to regulate fluid flow through a fluid network and may be a bi-directional valve, a check valve, and/or a vent, among others. For example, a valve may be used to block or permit fluid flow through a fluid passage, that is, as a binary switch, and/or to adjust the rate of fluid flow. Accordingly, operation of a valve may select a portion of a fluid network that is active, may isolate one or more portions of the fluid network, and/or may select a processing step that is implemented, among others. Therefore, valves may be positioned and operated to deliver fluid, reagents, and/or sample(s) from a fluid compartment to a desired region of a fluid network. Suitable valves may include movable diaphragms or membranes, compressible or movable passage walls, ball valves, sliding valves, flap valves, bubble valves, and/or immiscible fluids, among others. Such valves may be operated by a solenoid, a motor, pressure (see above), a heater, and/or the like.

Suitable valves may be microvalves formed on (or in) substrates along with thin-film electronic devices (see below) by conventional fabrication methods. Microvalves may be actuated by electrostatic force, piezoelectric force, and/or thermal expansion force, among others, and may have internal or external actuators. Electrostatic valves may include, for example, a polysilicon membrane or a polyimide cantilever that is operable to cover a hole formed in a substrate. Piezoelectric valves may include external (or internal) piezoelectric disks or beams that expand against a valve actuator. Thermal expansion valves may include a sealed pressure chamber bounded by a diaphragm. Heating the chamber causes the diaphragm to expand against a valve seat. Alternatively, thermal expansion valves may include a bubble valve. The bubble valve may be formed by a heater element that heats fluid to form a bubble in a passage so that the bubble blocks fluid flow through the passage. Discontinued heating collapses the bubble to allow fluid flow. Microvalves may be reversible, that is, capable of both closing and opening, or may be substantially irreversible, that is, single-use valves capable of only opening or closing. An exemplary single-use valve is a heat-sensitive obstruction in a fluid passage, for example, in a polyimide layer. Such an obstruction may be destroyed or modified upon heating to allow passage of fluid.

Vents may be used, for example, to allow release of displaced gas that results from fluid entering a fluid compartment. Suitable vents may include hydrophobic membranes that allow gas to pass but restrict passage of hydrophilic liquids. An exemplary vent is a GORETEX membrane.

A microfluidic device, as described herein, may be configured to perform or accommodate three steps: inputting, processing, and outputting. These steps are generally performed in order, for a given sample, but may be performed asynchronously when plural samples are inputted into the device.

Inputting allows a user of the microfluidic device to introduce sample(s) from the external world into the microfluidic device. Accordingly, inputting requires an interface(s) between the external world and the device. The interface thus typically acts as a port, and may be a septum, a valve, and/or the like. Alternatively, or in addition, sample(s) may be formed synthetically from reagents within the device. Reagents may be introduced by a user or during manufacture of the device. In a preferred embodiment, the reagents are introduced and sealed into the device or cartridge during manufacture.

The inputted sample(s) is then processed. Processing may include any sample manipulation or treatment that modifies a physical or chemical property of the sample, such as sample composition, concentration, and/or temperature. Processing may modify an inputted sample into a form more suited for analysis of analyte(s) in the sample, may query an aspect of the sample through reaction, may concentrate the sample, may increase signal strength, and/or may convert the sample into a detectable form. For example, processing may extract or release (for example, from cells or viruses), separate, purify, concentrate, and/or enrich (for example, by amplification) one or more analytes from an inputted sample. Alternatively, or in addition, processing may treat a sample or its analyte(s) to physically, chemically, and/or biologically modify the sample or its analyte(s). For example, processing may include chemically modifying the sample/analyte by labeling it with a dye, or by reaction with an enzyme or substrate, test reagent, or other reactive materials. Processing, also or alternatively, may include treating the sample/analyte(s) with a biological, physical, or chemical condition or agent. Exemplary conditions or agents include hormones, viruses, nucleic acids (for example, by transfection), heat, radiation, ultrasonic waves, light, voltage pulse(s), electric fields, particle irradiation, detergent, pH, and/or ionic conditions, among others. Alternatively, or in addition, processing may include analyte-selective positioning. Exemplary processing steps that selectively position analyte may include capillary electrophoresis, chromatography, adsorption to an affinity matrix, specific binding to one or more positioned receptors (such as by hybridization, receptor-ligand interaction, etc.), by sorting (for example, based on a measured signal), and/or the like.

Outputting may be performed after sample processing. A microfluidic device may be used for analytical and/or preparative purposes. Thus, the step of outputting generally includes obtaining any sample-related signal or material from the microfluidic device.

Sample-related signals may include a detectable signal that is directly and/or indirectly related to a processed sample and measured from or by the microfluidic device. Detectable signals may be analog and/or digital values, single or multiple values, time-dependent or time-independent values (e.g., steady-state or endpoint values), and/or averaged or distributed values (e.g., temporally and/or spatially), among others.

The detectable signal may be detected optically and/or electrically, among other detection methods. The detectable signal may be an optical signal(s), such as absorbance, luminescence (fluorescence, electroluminescence, bioluminescence, chemiluminescence), diffraction, reflection, scattering, circular dichroism, and/or optical rotation, among others. Suitable fluorescence methods may include fluorescence resonance energy transfer (FRET), fluorescence lifetime (FLT), fluorescence intensity (FLINT), fluorescence polarization (FP), total internal reflection fluorescence (TIRF), fluorescence correlation spectroscopy (FCS), fluorescence recovery after photobleaching (FRAP), and/or fluorescence activated cell sorting (FACS), among others. Optical signals may be measured as a nonpositional value, or set of values, and/or may have spatial information, for example, as measured using imaging methods, such as with a charge-coupled device. In some embodiments, the detectable signal may be an optoelectronic signal produced, for example, by an onboard photodiode(s). Other detectable signals may be measured by surface plasmon resonance, nuclear magnetic resonance, electron spin resonance, mass spectrometry, and/or the like. Alternatively, or in addition, the detectable signal may be an electrical signal(s), that is, a measured voltage, resistance, conductance, capacitance, power, etc. Exemplary electrical signals may be measured, for example, across a cell membrane, as a molecular binding event(s) (such as nucleic acid duplex formation, receptor-ligand interaction, etc.), and/or the like.

In some embodiments, the microfluidic device may be used for sample preparation. Sample-related material that may be outputted includes any chemical or biological compound(s), polymer(s), aggregate(s), mixture(s), assembli(es), and/or organism(s) that exits the device after processing. Such sample-related material may be a chemically modified (synthetic), biologically modified, purified, and/or sorted derivative, among others, of an inputted sample.

The microfluidic device may include distinct structural portions for fluid handling (and storage) and for conducting assays, as exemplified in Section II. These portions may be configured to carry out distinct processing and/or manipulation steps. The fluid-handling portion may be formed separately from the assay portion and may have a fluid network or fluid space that is more three-dimensional than the fluid network or fluid space of the assay portion. The fluid-handling portion may have fluid chambers with any suitable volume, including one or more chambers with a fluid capacity of tens or hundreds of microliters up to about five milliliters or more.

The fluid-handling portion may include a sample input site(s) (port) to receive sample, and plural fluid reservoirs to hold and deliver reagents and/or to receive waste. The fluid-handling portion may be dimensioned for somewhat larger volumes of fluid, in some cases, volumes of greater than one microliter or one milliliter. In addition, the fluid-handling portion may include a pre-processing site(s), formed by one or more fluid passages, to separate an analyte(s) of interest from waste material, for example, to isolate analytes (such as nucleic acids) from a sample that includes one or plural cells. The fluid-handling portion may define a generally nonplanar fluid network or fluid space. In a nonplanar or three-dimensional fluid network, one or more portions of the fluid network may be disposed greater than two millimeters from any common plane.

The assay portion may provide a site at which final sample processing occurs and/or assay signals are measured. The assay portion may be configured for manipulation and analysis of smaller sample volumes, generally having fluid chambers less than about 50 microliters, preferably less than about 10 microliters, and more preferably less than about one microliter.

The assay portion may be distinct from the fluid-handling portion, that is, formed of distinct components not shared with the fluid-handling portion. Accordingly, the assay portion may be formed separately, and then attached to the fluid-handling portion to fluidly connect fluid compartments of the portions.

The assay portion may include a substrate portion and a fluid barrier. The electronic circuitry may be disposed at least partially or at least substantially between the substrate and the fluid barrier. The substrate portion may cooperatively define a fluid space with the fluid barrier near a surface of the substrate portion. The electronic circuitry may include the thin-film portions or layers of an electronic circuit (or circuits), in which the thin-film layers also are disposed near the surface of the substrate. A structure that is near or proximate the surface is closer to the substrate surface than to an opposing surface of the substrate.

The electrical properties of the substrate may determine where the electronic circuitry, particularly solid-state electronic switching devices, is positioned relative to the substrate and the fluid barrier. The substrate may be a semiconductor so that some portions of the electronic circuitry are created within the substrate, for example, by n- and p-doping. Alternatively, the substrate may be an insulator. In this case, all of the electronic circuitry may be carried external to the substrate. A suitable substrate may be generally flat or planar on a pair of opposing surfaces, for example, to facilitate deposition of thin films. The substrate may be at least substantially inorganic, including as silicon, gallium arsenide, germanium, glass, ceramic, alumina, and/or the like.

Thin-film electronic circuitry includes thin films or thin-film layers. Each thin-film layer of the electronic circuitry may play a direct or auxiliary role in operation of the circuitry, that is, a conductive, insulating, resistive, capacitive, gating, and/or protective role, among others. The protective and/or insulating role may provide electrical insulation, chemical insulation to prevent fluid-mediated corrosion, and/or the like. The thin-film layers may have a thickness of less than about 100 μm, 50 μm, or 20 μm. Alternatively, or in addition, the thin-film layers may have a thickness of greater than about 10 nm, 20 nm, or 50 nm. Such thin films form electronic devices, which are described as electronic because they are controlled electronically by the electronic circuitry of the assay portion. The electronic devices are configured to modify and/or sense a property of fluid within a fluid compartment of the assay portion. Thus, the electronic devices and portions of the thin-film layers may be disposed between the substrate and the fluid network or compartment of the assay portion. Exemplary modifying devices include electrodes, heaters (for example, resistors), coolers, pumps, valves, and/or so on. Accordingly, the modified property may be analyte distribution or position within the fluid or fluid compartment, analyte mobility, analyte concentration, analyte abundance relative to related sample components, fluid flow rate, fluid isolation, or fluid/analyte temperature, among others. Alternatively, or in addition, thin-film devices may monitor or sense fluid and/or analyte conditions or positions. Exemplary sensing devices may include temperature sensors, flow-rate sensors, pH sensors, pressure sensors, fluid sensors, optical sensors, current sensors, voltage sensors, analyte sensors, and/or the like. Combining a modifying and a sensing device may allow feedback control, for example, closed loop temperature control of a fluid region within the assay portion.

Electronic circuitry included in the assay portion is flexible, in contrast to electrical circuits that respond linearly. Electronic circuits use semiconductor devices (transistors, diodes, etc.) and solid-state electronic switching so that a smaller number of input-output lines can connect electrically to a substantially greater number of electronic devices. Accordingly, the electronic circuitry may be connected to and/or may include any suitable combination of input and output lines, including power/ground lines, data input lines, fire pulse lines, data output lines, and/or clock lines, among others. Power/ground lines may provide power to modifying and sensing devices. Data input lines may provide data indicative of devices to be turned on (for example, a heater(s) or electrode(s)). Fire pulse lines may be supplied externally or internally to the chip. These lines may be configured to cause activation of a particular set of data for activating modifying and/or sensing devices. Data output lines may receive data from circuitry of the assay portion, for example, digital data from sensing devices. Based on the rate of data input and output, a single data input/output line or plural data input/output lines may be provided. With a low data rate, the single data input/output line may be sufficient, but with a higher rate, for example, to drive plural thin-film devices in parallel, one or more data input lines and a separate data input/output line may be necessary. Clock lines may provide timing of processes, such as sending and receiving data from a controller (see below).

A microfluidic device may be configured to be controlled by a control apparatus or controller. Accordingly, the microfluidic device is electrically coupled to the controller, for example, conductively, capacitively, and/or inductively. The controller may provide any of the input and/or output lines described above. In addition, the controller may provide a user interface, may store data, may provide one or more detectors, and/or may provide a mechanical interface, Exemplary functions of the controller include operating and/or providing valves, pumps, sonicators, light sources, heaters, coolers, and/or so on, in order to modify and/or sense fluid, sample, and/or analyte in the microfluidic device.

Further aspects of microfluidic devices, fluid-handling portions, assay portions, and controllers, among others, are described above in Section II.

IV. Samples

Microfluidic systems, as described herein, are configured to process samples. A sample generally includes any material of interest that is received and processed by a microfluidic system, either to analyze the material of interest (or analyte) or to modify it for preparative purposes. The sample generally has a property or properties of interest to be measured by the system or is advantageously modified by the system (for example, purified, sorted, derivatized, cultured, etc.). The sample may include any compound(s), polymer(s), aggregate(s), mixture(s), extract(s), complex(es), particle(s), virus(es), cell(s), and/or combination thereof. The analytes and/or materials of interest may form any portion of a sample, for example, being a major, minor, or trace component in the sample.

Samples, and thus analytes contained therein, may be biological. Biological samples generally include cells, viruses, cell extracts, cell-produced or -associated materials, candidate or known cell modulators, and/or man-made variants thereof. Cells may include eukaryotic and/or prokaryotic cells from any single-celled or multi-celled organism and may be of any type or set of types. Cell-produced or cell-associated materials may include nucleic acids (DNA or RNA), proteins (for example, enzymes, receptors, regulatory factors, ligands, structural proteins, etc.), hormones (for example, nuclear hormones, prostaglandins, leukotrienes, nitric oxide, cyclic nucleotides, peptide hormones, etc.), carbohydrates (such as mono-, di-, or polysaccharides, glycans, glycoproteins, etc.), ions (such as calcium, sodium, potassium, chloride, lithium, iron, etc.), and/or other metabolites or cell-imported materials, among others.

Biological samples may be clinical samples, research samples, environmental samples, forensic samples, and/or industrial samples, among others. Clinical samples may include any human or animal samples obtained for diagnostic and/or prognostic purposes. Exemplary clinical samples may include blood (serum, whole blood, or cells), lymph, urine, feces, gastric contents, bile, semen, mucus, a vaginal smear, cerebrospinal fluid, saliva, perspiration, tears, skin, hair, a tissue biopsy, a fluid aspirate, a surgical sample, a tumor, and/or the like. Research samples may include any sample related to biological and/or biomedical research, such as cultured cells or viruses (wild-type, engineered, and/or mutant, among others.), extracts thereof, partially or fully purified cellular material, material secreted from cells, material related to drug screens, etc. Environmental samples may include samples from soil, air, water, plants, and/or man-made structures, among others, being analyzed or manipulated based on a biological aspect.

Samples may be nonbiological. Nonbiological samples generally include any sample not defined as a biological sample. Nonbiological samples may be analyzed for presence/absence, level, size, and/or structure of any suitable inorganic or organic compound, polymer, and/or mixture. Suitable nonbiological samples may include environmental samples (such as samples from soil, air, water, etc.), synthetically produced materials, industrially derived products or waste materials, and/or the like.

Samples may be solid, liquid, and/or gas. The samples may be pre-processed before introduction into a microfluidic system or may be introduced directly. Pre-processing external to the system may include chemical treatment, biological treatment (culturing, hormone treatment, etc.), and/or physical treatment (for example, with heat, pressure, radiation, ultrasonic disruption, mixing with fluid, etc.). Solid samples (for example, tissue, soil, etc.) may be dissolved or dispersed in fluid before or after introduction into a microfluidic device and/or analytes of interest may be released from the solid samples into fluid within the microfluidic system. Liquid and/or gas samples may be pre-processed external to the system and/or may be introduced directly.

V. Assays

Microfluidic systems may be used to assay (analyze/test) an aspect of an inputted sample. Any suitable aspect of a biological or nonbiological sample may be analyzed by a microfluidic system. Suitable aspects may relate to a property of one or more analytes carried by the sample. Such properties may include presence/absence, level (such as level of expression of RNA or protein in cells), size, structure, activity (such as enzyme or biological activity), location within a cell, cellular phenotype, and/or the like. Structure may include primary structure (such as a nucleotide or protein sequence, polymer structure, isomer structure(s), or a chemical modification, among others), secondary or tertiary structure (such as local folding or higher order folding), and/or quaternary structure (such as intermolecular interactions). Cellular phenotypes may relate to cell state, electrical activity, cell morphology, cell movement, cell identity, reporter gene activity, and/or the like.

Microfluidic assays may measure presence/absence or level of one or more nucleic acid. Each nucleic acid analyzed may be present as a single molecule or, more typically, plural molecules. The plural molecules may be identical or substantially identical and/or may share a region, generally of twenty or more contiguous bases, that is identical. As used herein, a nucleic acid (nucleic acid species) generally includes a nucleic acid polymer or polynucleotide, formed as a chain of covalently linked monomer subunits. The monomer subunits may form polyribonucleic acids (RNA) and/or polydeoxyribonucleic acids (DNA) including any or all of the bases adenine, cytosine, guanine, uracil, thymine, hypoxanthine, xanthine, or inosine. Alternatively, or in addition, the nucleic acids may be natural, or synthetic derivatives, for example, including methylated bases, peptide nucleic acids, sulfur-substituted backbones, and/or the like. Nucleic acids may be single, double, and/or triple-stranded, and may be wild-type, or recombinant, deletion, insertion, inversion, rearrangement, and/or point mutants thereof.

Nucleic acid analyses may include testing a sample to measure the presence/absence, quantity, size, primary sequence, integrity, modification, and/or strandedness of one or more nucleic acid species (DNA and/or RNA) in the sample. Such analyses may provide genotyping information and/or may measure gene expression from a particular gene(s) or genetic region(s), among others.

Genotyping information may be used for identification and/or quantitation of microorganisms, such as pathogenic species, in a sample. Exemplary pathogenic organisms may include, but are not limited to, viruses, such as HIV, hepatitis virus, rabies, influenza, CMV, herpesvirus, papilloma viruses, rhinoviruses; bacteria, such as *S. aureus, C. perfringens, V. parahaemolyticus, S. typhimurium, B. anthracis, C. botulinum, E. coli*, and so on; fungi, such as those included in the genuses *Candida, Coccidioides, Blastomyces, Histoplasma, Aspergillus, Zygomycetes, Fusarium* and *Trichosporon*, among others; and protozoans, such as *Plasmodia* (for example, *P. vivax, P. falciparum*, and *P. malariae*, etc.), *G. lamblia, E. histolitica, Cryptosporidium*, and *N. fowleri*, among others. The analysis may determine, for example, if a person, animal, plant, food, soil, or water is infected with or carries a particular microorganism(s). In some cases, the analysis may also provide specific information about the particular strain(s) present.

Genotyping analysis may include genetic screening for clinical or forensic analysis, for example, to determine the presence/absence, copy number, and/or sequence of a particular genetic region. Genetic screening may be suitable for prenatal or postnatal diagnosis, for example, to screen for birth defects, identify genetic diseases and/or single-nucleotide polymorphisms, or to characterize tumors. Genetic screening also may be used to assist doctors in patient care, for example, to guide drug selection, patient counseling, etc. Forensic analyses may use genotyping analysis, for example, to identify a person, to determine the presence of a person at a crime scene, or to determine parentage, among others. In some embodiments, nucleic acids may carry and/or may be analyzed for single nucleic polymorphisms.

Microfluidic systems may be used for gene expression analysis, either quantitatively (amount of expression) or qualitatively (expression present or absent). Gene expression analysis may be conducted directly on RNA, or on complementary DNA synthesized using sample RNA as a template, for example, using a reverse transcriptase enzyme. The complementary DNA may be synthesized within a microfluidic device, such as the embodiment described in Section II, for example, in the assay portion, or external to the device, that is, prior to sample input.

Expression analysis may be beneficial for medical purposes or research purposes, among others. For example, expression analysis of individual genes or sets of genes (profiling) may be used to determine or predict a person's health, guide selection of a drug(s) or other treatment, etc. Alternatively, or in addition, expression may be useful in research applications, such as reporter gene analysis, screening libraries (for example, libraries of chemical compounds, peptides, antibodies, phage, bacteria, etc.), and/or the like.

Assays may involve processing steps that allow a property of an analyte to be measured. Such processing steps may include labeling, amplification, binding to a receptor(s), and/or so on.

Labeling may be carried out to enhance detectability of the analyte. Suitable labels may be covalently or noncovalently coupled to the analyte and may include optically detectable dyes (fluorophores, chromophores, energy transfer groups, etc.), members of specific binding pairs (SBPs, such as biotin, digoxigenin, epitope tags, etc.; see Table 1), and/or the like. Coupling of labels may be conducted by an enzymatic reaction, for example, nucleic acid-templated replication (or ligation), protein phosphorylation, and/or methylation, among others, or may be conducted chemically, biologically, or physically (for example, light- or heat-catalyzed, among others).

For nucleic acid analyses, amplification may be performed to enhance sensitivity of nucleic acid detection. Amplification is any process that selectively increases the abundance (number of molecules) of a target nucleic acid species, or a region within the target species. Amplification may include thermal cycling (for example, polymerase chain reaction, ligase chain reaction, and/or the like) or may be isothermal (for example, strand displacement amplification). Further aspects of amplification are described above in Section II.

Receptor binding may include contacting an analyte (or a reaction product templated by, or resulting from, the presence of the analyte) with a receptor that specifically binds the analyte. The receptor(s) may be attached to, or have a fixed position within, a microfluidic compartment, for example, in an array, or may be distributed throughout the compartment. Specific binding means binding that is highly selective for the intended partner in a mixture, generally to the exclusion of binding to other moieties in the mixture. Specific binding may be characterized by a binding coefficient of less than about $10^{-4}$ M, and preferred specific binding coefficients are less than about $10^{-5}$ M, $10^{-7}$ M, or $10^{-9}$ M. Exemplary specific binding pairs that may be suitable for receptor-analyte interaction are listed below in Table 1.

TABLE 1

Representative Specific Binding Pairs

| First SBP Member | Second SBP Member |
|---|---|
| biotin | avidin or streptavidin |
| antigen | antibody |
| carbohydrate | lectin or carbohydrate receptor |
| DNA | antisense DNA; protein |
| enzyme substrate | enzyme; protein |
| histidine | NTA (nitrilotriacetic acid) |
| IgG | protein A or protein G |
| RNA | antisense or other RNA; protein |

Further aspects of sample assays, particularly assay of nucleic-acid analytes in samples, are described above in Sections I and II.

It is believed that the disclosure set forth above encompasses multiple distinct embodiments of the invention. While each of these embodiments has been disclosed in specific form, the specific embodiments thereof as disclosed and illustrated herein are not to be considered in a limiting sense as numerous variations are possible. The subject matter of this disclosure thus includes all novel and nonobvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

What is claimed is:

1. A method of analyzing a nucleic acid target in a nucleic acid mixture of the target and non-target nucleic acids, the method comprising:
   - attracting the nucleic acid mixture in fluid to an electrode included in electronics formed on a substrate;
   - retaining the target selectively by binding the target to a receptor disposed near the electrode;
   - locally heating a portion of the fluid near the receptor to adjust a stringency under which the target binds to the receptor;
   - enriching the mixture for the target by removing unretained nucleic acids; and
   - amplifying the target from the enriched mixture.

2. The method of claim 1, wherein enriching includes moving the unretained nucleic acids at least partially by mechanically driven flow.

3. The method of claim 2, wherein moving is conducted under a binding stringency that is determined by at least one of heating and applying an electric field to the receptor.

4. The method of claim 1, wherein attracting and retaining are conducted in a first compartment, amplifying being conducted in a distinct second compartment.

5. The method of claim 4, further comprising moving the target from the first compartment to the second compartment after the step of enriching and before the step of amplifying.

6. The method of claim 1, further comprising detecting the amplified target.

7. The method of claim 1, the receptor being a nucleic acid that is at least substantially complementary to the target, the nucleic acid being connected to the electrode.

8. The method of claim 1, amplifying being conducted with nucleic acid primers that are each distinct from the receptor.

9. The method of claim 1, wherein the receptor is a first receptor, the method further comprising contacting a second receptor with the amplified target to assay the amplified target, the second receptor being configured to selectively bind the target.

10. The method of claim 9, each of retaining and contacting being performed with a binding stringency, the stringency of contacting being greater than the stringency of retaining.

11. The method of claim 9, the first and second receptors being identical.

12. The method of claim 11, enriching and contacting being conducted In a shared compartment.

13. The method of claim 9, amplifying and contacting being conducted in different compartments.

14. The method of claim 9, the first and second receptors being distinct structurally and separated spatially.

15. The method of claim 1, further comprising releasing the retained target before the step of amplifying.

16. A microfluidic device for analyzing a nucleic acid target in a nucleic acid mixture of the target and non-target nucleic acids, comprising:

a substrate portion at least partially defining fluidically connected first and second chambers, the substrate portion including a substrate and electronics formed on the substrate, the electronics including a first electrode operable to form an electric field in the first chamber and a second electrode operable to form an electric field in the second chamber, the electronics also including a plurality of heating devices operable to adjust binding stringency locally in at least one of the first and second chambers; and first and second receptors for specifically binding the target, the first and second receptors being connected to the first and second electrodes, respectively.

17. The device of claim 16, the first and second receptors being distinct.

18. The device of claim 16, at least one of the heating devices being operable to reverse binding of the first receptor to the target.

19. The device of claim 16, further comprising a fluid-handling portion connected to the substrate portion and configured to move fluid to and receive fluid from the first chamber.

20. The device of claim 19, the fluid-handling portion being configured to move fluid at least partially by mechanically driven flow.

21. The device of claim 16, at least one of the first and second electrodes being plural electrodes.

* * * * *

UNITED STATES PATENT AND TRADEMARK OFFICE

CERTIFICATE OF CORRECTION

PATENT NO. : 7,217,542 B2
APPLICATION NO. : 10/286104
DATED : May 15, 2007
INVENTOR(S) : David Tyvoll et al.

It is certified that error appears in the above-identified patent and that said Letters Patent is hereby corrected as shown below:

In column 14, line 24, delete "templatedirected" and insert -- template-directed --, therefor.

In column 19, lines 53-54, delete "Section 111." and insert -- Section III. --, therefor.

In column 35, line 8, in Claim 12, delete "In" and insert -- in --, therefor.

Signed and Sealed this

Second Day of December, 2008

JON W. DUDAS
*Director of the United States Patent and Trademark Office*